US009775497B2

(12) United States Patent
Igarashi et al.

(10) Patent No.: US 9,775,497 B2
(45) Date of Patent: *Oct. 3, 2017

(54) ENDOSCOPE APPARATUS FOR OUTPUTTING SIGNALS CORRESPONDING TO FIRST AND SECOND NARROWBAND WAVELENGTH BANDS

(71) Applicant: OLYMPUS CORPORATION, Tokyo (JP)

(72) Inventors: Makoto Igarashi, Hachioji (JP); Tetsuo Nonami, Hino (JP); Kenji Taira, Mountain View, CA (US)

(73) Assignee: OLYMPUS CORPORATION, Tokyo (JP)

( * ) Notice: Subject to any disclaimer, the term of this patent is extended or adjusted under 35 U.S.C. 154(b) by 342 days.

This patent is subject to a terminal disclaimer.

(21) Appl. No.: 14/550,147

(22) Filed: Nov. 21, 2014

(65) Prior Publication Data
US 2015/0105616 A1    Apr. 16, 2015

Related U.S. Application Data

(63) Continuation of application No. 13/909,389, filed on Jun. 4, 2013, now Pat. No. 8,939,901, which is a (Continued)

(30) Foreign Application Priority Data

Mar. 30, 2012   (JP) ................................. 2012-082288

(51) Int. Cl.
*A61B 1/06*   (2006.01)
*A61B 1/04*   (2006.01)
*A61B 1/00*   (2006.01)

(52) U.S. Cl.
CPC .............. *A61B 1/04* (2013.01); *A61B 1/0005* (2013.01); *A61B 1/00009* (2013.01); (Continued)

(58) Field of Classification Search
CPC ....... A61B 1/04; A61B 1/043; A61B 1/00009; A61B 1/0005; A61B 1/06; A61B 1/0638; A61B 1/0646; A61B 1/0684
See application file for complete search history.

(56) References Cited

U.S. PATENT DOCUMENTS 4,914,512 A * 4/1990 Sekiguchi .............. A61B 1/042
                                                                348/453
5,001,556 A   3/1991 Nakamura et al.
(Continued)

FOREIGN PATENT DOCUMENTS

EP    1 302 152 A1   4/2003
EP    1 880 658 A1   1/2008
(Continued)

OTHER PUBLICATIONS

International Search Report mailed Feb. 12, 2013 issued in International Application No. PCT/JP2012/078741.
(Continued)

*Primary Examiner* — John P Leubecker
(74) *Attorney, Agent, or Firm* — Scully, Scott, Murphy & Presser, P.C.

(57) ABSTRACT

An endoscope apparatus includes: a light source device radiating at least one or more illumination lights having a predetermined wavelength band to a subject; a CCD picking up an image of a return light from the subject based on radiation of the illumination light from the light source device; an image processing section outputting a first image signal of a first wavelength band having a peak wavelength of spectral characteristic, between a wavelength band
(Continued)

including a maximum value and a wavelength band at a minimum value with regard to an absorption characteristic of living tissue, after image pickup by the CCD; and an observation monitor performing image display on the basis of the first image signal.

6 Claims, 19 Drawing Sheets

Related U.S. Application Data continuation of application No. PCT/JP2012/078741, filed on Nov. 6, 2012.

(52) U.S. Cl.
 CPC ............... *A61B 1/043* (2013.01); *A61B 1/06* (2013.01); *A61B 1/0638* (2013.01); *A61B 1/0646* (2013.01); *A61B 1/0684* (2013.01)

(56) References Cited

U.S. PATENT DOCUMENTS

| | | | |
|---|---|---|---|
| 5,078,150 A * | 1/1992 | Hara | A61B 1/00009 348/70 |
| 7,226,412 B2 | 6/2007 | Ueno et al. | |
| 7,850,599 B2 * | 12/2010 | Takeuchi | A61B 1/05 600/109 |
| 8,279,275 B2 | 10/2012 | Gono et al. | |
| 8,301,229 B2 | 10/2012 | Gono et al. | |
| 2003/0176768 A1 | 9/2003 | Gono et al. | |
| 2005/0267374 A1 | 12/2005 | Yokomise et al. | |
| 2006/0211915 A1 | 9/2006 | Takeuchi et al. | |
| 2008/0018733 A1 | 1/2008 | Hasegawa | |
| 2011/0237883 A1 * | 9/2011 | Chun | A61B 1/0638 600/109 |
| 2011/0237885 A1 | 9/2011 | Matsubara | |
| 2012/0010465 A1 | 1/2012 | Erikawa et al. | |
| 2012/0157768 A1 | 6/2012 | Saito | |
| 2012/0197077 A1 | 8/2012 | Kaku | |
| 2012/0220840 A1 | 8/2012 | Morita et al. | |
| 2012/0253122 A1 | 10/2012 | Minetoma et al. | |
| 2013/0265401 A1 | 10/2013 | Igarashi et al. | |
| 2017/0131206 A1 * | 5/2017 | Li | G01N 21/645 |

FOREIGN PATENT DOCUMENTS

| | | |
|---|---|---|
| JP | 2002095635 A | 4/2002 |
| JP | 2005296200 A | 10/2005 |
| JP | 2006341077 A | 12/2006 |

OTHER PUBLICATIONS

U.S. Non-Final Office Action dated Mar. 21, 2014 issued in U.S. Appl. No. 13/909,389.
U.S. Final Office Action dated Jul. 10, 2014 issued in U.S. Appl. No. 13/909,389.

* cited by examiner

FIG.9

| DIAMETER OF CAPILLARY VESSEL CB (mm) | DIAMETER OF THICK BLOOD VESSEL BV (mm) | MAGNIFICATION (m) | VALUE OF EXPRESSION (11) (m$^{-1}$/M) | cm$^{-1}$/M | HbO$_2$ (nm) | Hb (nm) |
|---|---|---|---|---|---|---|
| 0.01 | 1 | 100 | 2325844 | $2.3 \times 10E+4$ | 586 | 594 |
| 0.1 | 1 | 10 | 1279214 | $1.3 \times 10E+4$ | 590 | 602 |
| 0.01 | 2 | 200 | 1331236 | $1.3 \times 10E+4$ | 590 | 602 |
| 0.1 | 2 | 20 | 788351 | $0.8 \times 10E+4$ | 594 | 614 |

ENDOSCOPE APPARATUS FOR OUTPUTTING SIGNALS CORRESPONDING TO FIRST AND SECOND NARROWBAND WAVELENGTH BANDS

CROSS REFERENCE TO RELATED APPLICATIONS

This application is a continuation application of U.S. patent application Ser. No. 13/909,389, filed on Jun. 4, 2013, which is a continuation application of PCT International Application No. PCT/JP2012/078741, filed on Nov. 6, 2012, which claims benefit of Japanese Application No. 2012-082288, filed in Japan on Mar. 30, 2012, the entire contents each of which are incorporated herein by reference.

BACKGROUND OF THE INVENTION

1. Field of the Invention

The present invention relates to an endoscope apparatus, and in particular to an endoscope apparatus capable of displaying a blood vessel inside a subject.

2. Description of the Related Art

Conventionally, various kinds of minimally invasive examinations and operations using an endoscope have been performed in a medical field. A surgeon can insert an endoscope into a body cavity, observe a subject which has been image-picked up by an image pickup apparatus provided at a distal end portion of an endoscope insertion section, and treats a lesioned part using a treatment instrument inserted in a treatment instrument channel as necessary. An operation using an endoscope is advantageous in that a bodily burden on a patient is not heavy because an abdominal operation is not performed.

An endoscope apparatus is configured including an endoscope, an image processing apparatus connected to the endoscope and an observation monitor. An image of a legion is picked up by an image pickup device provided at a distal end portion of an endoscope insertion section, and the image is displayed on the monitor. The surgeon can make a diagnosis or perform necessary treatment, looking at the image displayed on the monitor.

Some endoscope apparatuses are capable of not only performing normal light observation using a white color light but also performing special light observation using a special light such as an infrared light in order to observe an internal blood vessel.

In the case of an infrared endoscope apparatus, for example, indocyanine green (ICG) having an absorption peak characteristic in a near infrared light near a wavelength of 805 nm is injected into a patient's blood as medicine. Then, infrared lights near wavelengths of 805 nm and 930 nm are radiated to the subject from a light source device in a time division manner. A signal of a subject image picked up by a CCD is inputted to a processor of the infrared endoscope apparatus. As for such an infrared endoscope apparatus, an apparatus is proposed in which the processor allocates an image near the wavelength of 805 nm to a green signal (G) and allocates an image near the wavelength of 930 nm to a blue signal (B), and outputs the images to a monitor as disclosed in, for example, Japanese Patent Application Laid-Open Publication No. 2000-41942. Since the image of the infrared light near the image of 805 nm which is well-absorbed by the ICG is allocated to green, the surgeon can observe an infrared image during administration of ICG with high contrast.

SUMMARY OF THE INVENTION

An endoscope apparatus of an aspect of the present invention is provided with: an illumination section radiating at least one or more illumination lights having a predetermined wavelength band to a part under an epithelium of a living mucosa of a subject; an image pickup section picking up an image of a return light from the part under the epithelium of the living mucosa based on radiation of the illumination section; an image output section outputting a signal corresponding to a first wavelength band having a narrowband spectral characteristic and a signal corresponding to a second wavelength band having a lower absorption coefficient of a hemoglobin absorption characteristic than an absorption coefficient of a hemoglobin absorption characteristic of the signal corresponding to the first wavelength band and having such a spectral characteristic that a scattering characteristic of the living tissue is suppressed, in a red band in a visible range, which is between a wavelength band including a maximum value and a wavelength band including a minimum value with regard to the hemoglobin absorption characteristic of the living tissue of the subject, after image pickup by the image pickup section; and a display section displaying an image on the basis of the signal corresponding to the first wavelength band and the signal corresponding to the second wavelength band.

BRIEF DESCRIPTION OF THE DRAWINGS

FIG. 9 is a table showing a result of calculation for combinations between cases where diameter of a capillary vessel CB is 0.01 mm and 0.1 mm and cases where diameter of a thick blood vessel BV is 1 mm and 2 mm, according to the first embodiment of the present invention;

DETAILED DESCRIPTION OF THE PREFERRED EMBODIMENTS

Embodiments of the present invention will be described below with reference to drawings.
(First Embodiment)
(Configuration of Endoscope Apparatus)

An embodiment of the present invention will be described below with reference to drawings.

Figure 1:
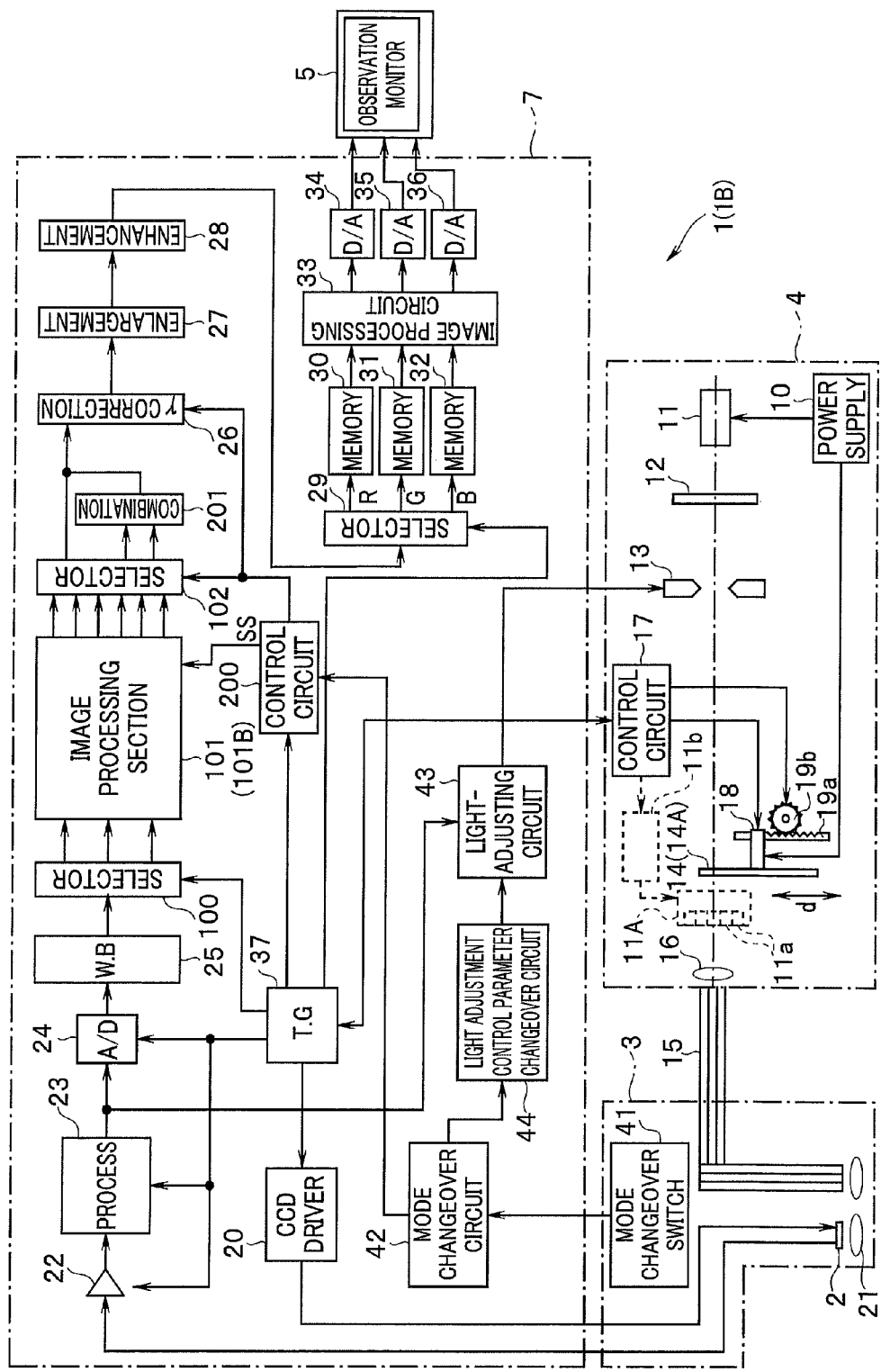
FIG. 1 is a configuration diagram showing a configuration of an endoscope apparatus according to a first embodiment of the present invention.

First, a configuration of an endoscope apparatus according to the present embodiment will be described. FIG. 1 is a configuration diagram showing the configuration of the endoscope apparatus according to the present embodiment.

As shown in FIG. 1, an endoscope apparatus 1 of the present embodiment is configured with an electronic endoscope 3 having a CCD 2, which is an image pickup device, as biological image information acquiring means or a living body image information acquiring section to be inserted into a body cavity to pick up an image of intra-body cavity tissue, a light source device 4 which supplies an illumination light to the electronic endoscope 3, and a video processor 7 which performs signal processing of an image pickup signal from the CCD 2 of the electronic endoscope 3 and displays an endoscopic image on an observation monitor 5. The endoscope apparatus 1 has two modes of a normal light observation mode and a narrowband light observation mode. Note that, in the description below, since the normal light observation mode of the endoscope apparatus 1 is the same as a conventional normal light observation mode, description of a configuration of the normal light observation mode is omitted, and the narrowband light observation mode will be mainly described.

The CCD 2 constitutes an image pickup section or image pickup means for receiving a return light of an illumination light radiated to a subject to pick up an image of the subject.

The light source device 4 as illumination means is configured being provided with a xenon lamp 11 which emits an illumination light (white color light), a heat ray cut filter 12 which cuts off a heat ray of the white color light, a diaphragm device 13 which controls a light amount of the white color light via the heat ray cut filter 12, a rotating filter 14 as band limiting means or a band limiting section which causes the illumination light to be frame-sequential lights, a condensing lens 16 which collects the frame-sequential lights via the rotating filter 14 on an incident face of a light guide 15 arranged in the electronic endoscope 3, and a control circuit 17 which controls rotation of the rotating filter 14. The xenon lamp 11, the rotating filter 14 and the light guide 15 constitute an irradiating section or irradiating means that illuminates the subject with the illumination light.

Figure 2:
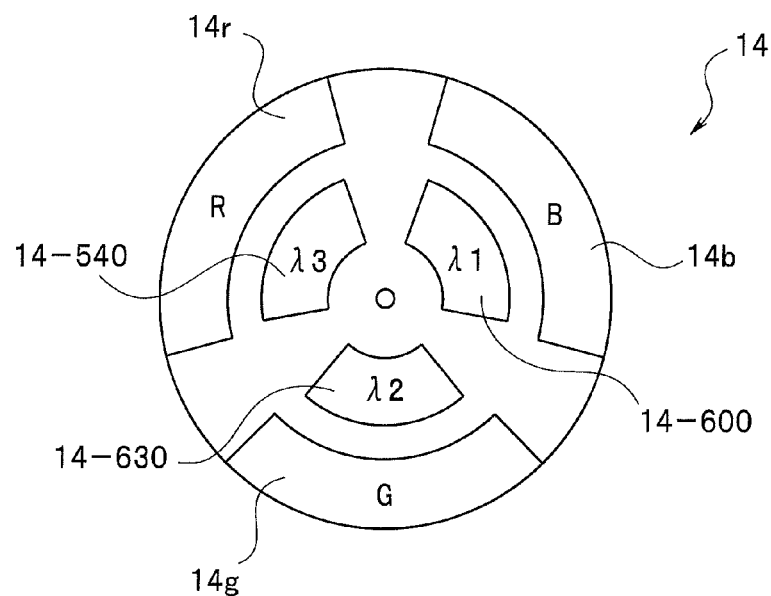
FIG. 2 is a diagram showing a configuration of a rotating filter 14 according to the first embodiment of the present invention.

FIG. 2 is a diagram showing a configuration of the rotating filter 14. The rotating filter 14 is a filter which transmits a light from the xenon lamp 11 which is a light source. The rotating filter 14 as a wavelength band limiting section or wavelength band limiting means is configured in a disc shape as shown in FIG. 2 and with a structure having a rotating shaft at the center. The rotating filter 14 has two filter groups. On an outer circumferential side of the rotating filter 14, an R (red) filter section 14r, a G (green) filter section 14g and a B (blue) filter section 14b constituting a filter set for outputting frame-sequential lights having a spectral characteristic for normal light observation are arranged along a circumferential direction as a first filter group.

On an inner circumferential side of the rotating 14, three filters 14-600, 14-630 and 14-540 that transmit lights having three predetermined narrowband wavelengths are arranged along the circumferential direction as a second filter group.

The filter 14-600 is configured to transmit a light near a wavelength of 600 nm (λ1) as a narrowband light. The filter 14-630 is configured to transmit a light near a wavelength of 630 nm (λ2) as a narrowband light. The filter 14-540 is configured to transmit a light near a wavelength of 540 nm (λ1) as a narrowband light.

In the case of near the wavelength of 600 nm, "near" means that the light is a narrowband light having a center wavelength of 600 nm and having a distribution in a range of a width of, for example, 20 nm with the wavelength of 600 nm as the center (i.e., from a wavelength of 590 nm before the wavelength of 600 nm to a wavelength of 610 nm after the wavelength of 600 nm). The same goes for the other wavelengths, the wavelength of 630 nm and the wavelength of 540 nm to be described later.

The rotating filter 14 is arranged on an optical path extending from the xenon lamp 11, which is a section of emitting an illumination light, to an image pickup surface of the CCD 2. The rotating filter 14 limits at least one (here, three) wavelength band among multiple wavelength bands of the illumination light to be narrowed in each mode.

The control circuit 17 controls a motor 18 for causing the rotating filter 14 to rotate to control the rotation of the rotating filter 14.

A rack 19a is connected to the motor 18. A motor not shown is connected to a pinion 19b. The rack 19a is attached to be screwed with the pinion 19b. The control circuit 17 can move the rotating filter 14 in a direction indicated by an arrow d by controlling rotation of the motor connected to the pinion 19b. Therefore, the control circuit 17 controls the motor connected to the pinion 19b so that, according to a mode switching operation by the user to be described later, the first filter group is positioned on the optical path in the normal light observation mode, and the second filter group in the narrowband light observation mode.

Note that, electric power is supplied from a power supply section 10 to the xenon lamp 11, the diaphragm device 13, the rotating filter motor 18, and the motor (not shown) connected to the pinion 19b.

Thus, the light source device 4 constitutes illumination means or an illumination section that radiates at least one or more illumination lights (here, three narrowband lights) having a predetermined wavelength band to a subject in the narrowband light observation mode. Here, one of the three illumination lights is a narrowband light for clearly displaying a blood vessel in a deep part 1 to 2 mm from a mucosal epithelium part, and the other two are a narrowband light for displaying a blood vessel in a deeper part and a narrowband light for displaying capillary vessels within a range near the epithelium part. Therefore, the light source device 4 is the illumination means or the illumination section that radiates at least one or more illumination lights via the band limiting means or the band limiting section that limits a wavelength band to a first wavelength band (to be described later) in the narrowband light observation mode.

The video processor 7 includes a CCD driving circuit 20 which is a CCD driver, an amplifier 22, a process circuit 23, an A/D converter 24, a white balance circuit (hereinafter referred to as W. B) 25, a selector 100, an image processing section 101, a selector 102, a γ correction circuit 26, an enlargement circuit 27, an emphasis circuit 28, a selector 29, synchronizing memories 30, 31 and 32, and 33, an image processing circuit 33, D/A converters 34, 35 and 36, a timing generator (hereinafter referred to as T. G) 37, a mode changeover circuit 42, a light-adjusting circuit 43, a light adjustment control parameter changeover circuit 44, a control circuit 200, and a combination circuit 201 as display image generating means or a displayed image generating section.

The CCD driving circuit 20 drives the CCD 2 provided in the electronic endoscope 3 and causes the CCD 2 to output frame-sequential image pickup signals synchronized with rotation of the rotating filter 14. The amplifier 22 amplifies the frame-sequential image pickup signals obtained by picking up an image of intra-body cavity tissue by the CCD 2 via an objective optical system 21 provided at a distal end of the electronic endoscope 3.

Note that a polarizing plate may be arranged on each of a front face of the CCD 2, which is an image pickup device, and a front face of the light guide 15, in a crossed Nichol prism state. By two polarizing ends in the crossed Nichol prism state, the CCD 2 can pick up an image of a light mainly from a deep mucosa without receiving a light reflected from a mucosal surface.

The process circuit 23 performs correlated double sampling, noise removal and the like for the frame-sequential image pickup signals via the amplifier 22. The A/D converter 24 converts the frame-sequential image pickup signals having passed through the process circuit 23 to digital frame-sequential image signals.

The W. B 25 performs gain adjustment and executes white balance processing for the frame-sequential image signals digitized by the A/D converter 24 so that, for example, brightness of an R signal of the image signal and brightness of a B signal of the image signal are equal with each other with reference to a G signal of the image signal.

Note that white balance adjustment at the W. B 25 is performed with reference to luminance of a return light of a narrowband light near the wavelength of 600 nm.

The selector 100 distributes and outputs frame-sequential image signals from the W. B 25 to respective sections in the image processing section 101.

The image processing section 101 is an image signal processing section or image signal processing means that converts an RGB image signal for normal light observation or three image signals for narrowband light observation from the selector 100 to an image signal for display. The image processing section 101 outputs, according to a selection signal SS from the control circuit 200 based on a mode signal, image signals in the normal light observation mode and in the narrowband light observation mode to the selector 102.

The selector 102 sequentially outputs frame-sequential image signals of the image signal for normal light observation and the image signal for narrowband light observation from the image processing section 101 to the γ correction circuit 26 and the combination circuit 201.

The γ correction circuit 26 applies γ correction processing to the frame-sequential image signals from the selector 102 or the combination circuit 201. The enlargement circuit 27 performs enlargement processing of the frame-sequential image signals which have been γ-correction-processed by the γ correction circuit 26. The emphasis circuit 28 applies edge emphasis processing to the frame-sequential image signals which have been enlargement-processed by the enlargement circuit 27. The selector 29 and the synchronizing memories 30, 31 and 32 are for synchronizing the frame-sequential image signals from the emphasis circuit 28.

The image processing circuit 33 reads out respective frame-sequential image signals stored in the synchronizing memories 30, 31 and 32 and performs moving image color shift correction processing and the like. The D/A converters 34, 35 and 36 convert the image signals from the image processing circuit 33 into RGB analog video signals and output the RGB analog video signals to the observation monitor 5. The T. G 37 inputs a synchronization signal synchronized with the rotation of the rotating filter 14, from the control circuit 17 of the light source device 4, and outputs various timing signals to the respective circuits in the video processor 7 described above.

In the electronic endoscope 2, a mode changeover switch 41 for switching between the normal light observation mode and the narrowband light observation mode is provided. An output of this mode changeover switch 41 is outputted to the mode changeover circuit 42 in the video processor 7. The mode changeover circuit 42 of the video processor 7 outputs a control signal to a light adjustment control parameter changeover circuit 44 and the control circuit 200. The light-adjusting circuit 43 controls the diaphragm device 13 of the light source device 4 on the basis of light adjustment control parameters from the light adjustment control parameter changeover circuit 44 and an image pickup signal which has passed through the process circuit 23 to perform proper brightness control.

Each circuit in the video processor 7 executes predetermined processing corresponding to a specified mode. Processing corresponding to each of the normal light observation mode and the narrowband light observation mode is executed, and an image for normal light observation or an image for narrowband light observation is displayed on the observation monitor 5. The observation monitor 5 is display means or a display section that displays an image on the basis of an image signal of a relatively thick blood vessel with a diameter of about 1 to 2 mm in a deep mucosa about 1 to 2 mm from a mucosal epithelium part.

(Whole Process Flow of Narrowband Light Observation)

Next, an overall rough flow of the narrowband light observation in the present embodiment will be briefly described below.

Figure 3:
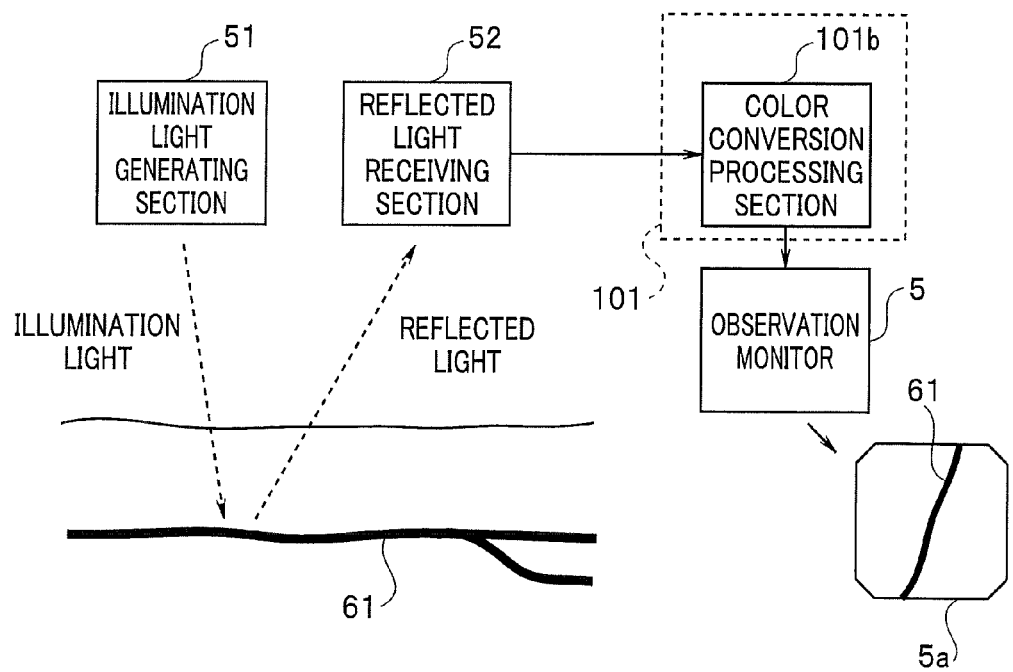
FIG. 3 is a diagram for illustrating a whole process flow in narrowband light observation according to the first embodiment of the present invention.

FIG. 3 is a diagram for illustrating a whole process flow in the narrowband light observation according to the present embodiment.

A surgeon inserts the insertion section of the endoscope into a body cavity and positions the distal end portion of the insertion section of the endoscope near a lesioned part under the normal light observation mode. When confirming the treatment target lesioned part, the surgeon operates the mode changeover switch 41 to switch the endoscope apparatus 1 to the narrowband light observation mode in order to observe a relatively thick blood vessel in a deep part having a diameter of, for example, 1 to 2 mm, and running from a submucosa to a muscularis propria.

Under the narrowband light observation mode, the control circuit 17 of the endoscope apparatus 1 controls the motor connected to the pinion 19*b* to move the position of the rotating filter 14 so that a light transmitted through the second filter group is emitted from the light source device 4. Furthermore, the control circuit 200 also controls the various circuits in the video processor 7 to perform image processing for observation by a narrowband wavelength.

As shown in FIG. 3, in the narrowband light observation mode, an illumination light having a narrowband wavelength is emitted from the distal end portion of the insertion section of the endoscope 3, from an illumination light generating section 51, transmitted through a stratum mucosum, and radiated to a blood vessel 61 running in a submucosa and a muscularis propria. Here, the illumination light generating section 51 is configured including the light source device 4, the rotating filter 14, the light guide 15, and the like, and emits an illumination light from the distal end of the endoscope insertion section. By rotation of the rotating filter 14, a narrowband light near the wavelength of 600 nm, a narrowband light near the wavelength of 630 nm and a narrowband light near the wavelength of 540 nm are successively and sequentially emitted from the light source device 4 and radiated to a subject.

Each of reflected lights of the narrowband light near the wavelength of 600 nm, the narrowband light near the wavelength of 630 nm and the narrowband light near the wavelength of 540 nm is received by a reflected light receiving section 52 which is the CCD 2. The CCD 2 outputs image pickup signals of the respective reflected lights, and supplied to the selector 100 via the amplifier 22 and the like. The selector 100 holds a first image signal P1 near the wavelength of 600 nm, a second image signal P2 near the wavelength of 630 nm and a third image signal P3 near the wavelength of 540 nm and supplies the images to the image processing section 101 according to a predetermined timing from the T. G 37. The image processing section 101 includes a color conversion processing section 101*b* for the narrowband light observation mode.

For example, in ESD in which, for example, a stratum mucosum of an inner wall of a digestive tract such as a stomach, a gullet and a large bowel, where a lesioned part exists, is dissected and ablated with the use of the endoscope apparatus 1, the surgeon has to be careful not to cut a relatively thick blood vessel in tissue with an electric surgical knife or the like. When setting the endoscope apparatus 1 to the narrowband light observation mode, the surgeon can clearly depict blood vessels under the surface of living tissue.

The color conversion processing section 101*b* of the image processing section 101 in FIG. 1 allocates each image signal to each channel of RGB of the observation monitor 5 and supplies the image signal to the selector 102. As a result, the relatively thick blood vessel 61 in a deep mucosa is displayed with high contrast on a screen 5*a* of the observation monitor 5. Thereby, the surgeon can apply the ESD to the lesioned part while paying attention to the blood vessel 61 running in the submucosa and the muscularis propria, which is displayed on the observation monitor 5.

Figure 4:
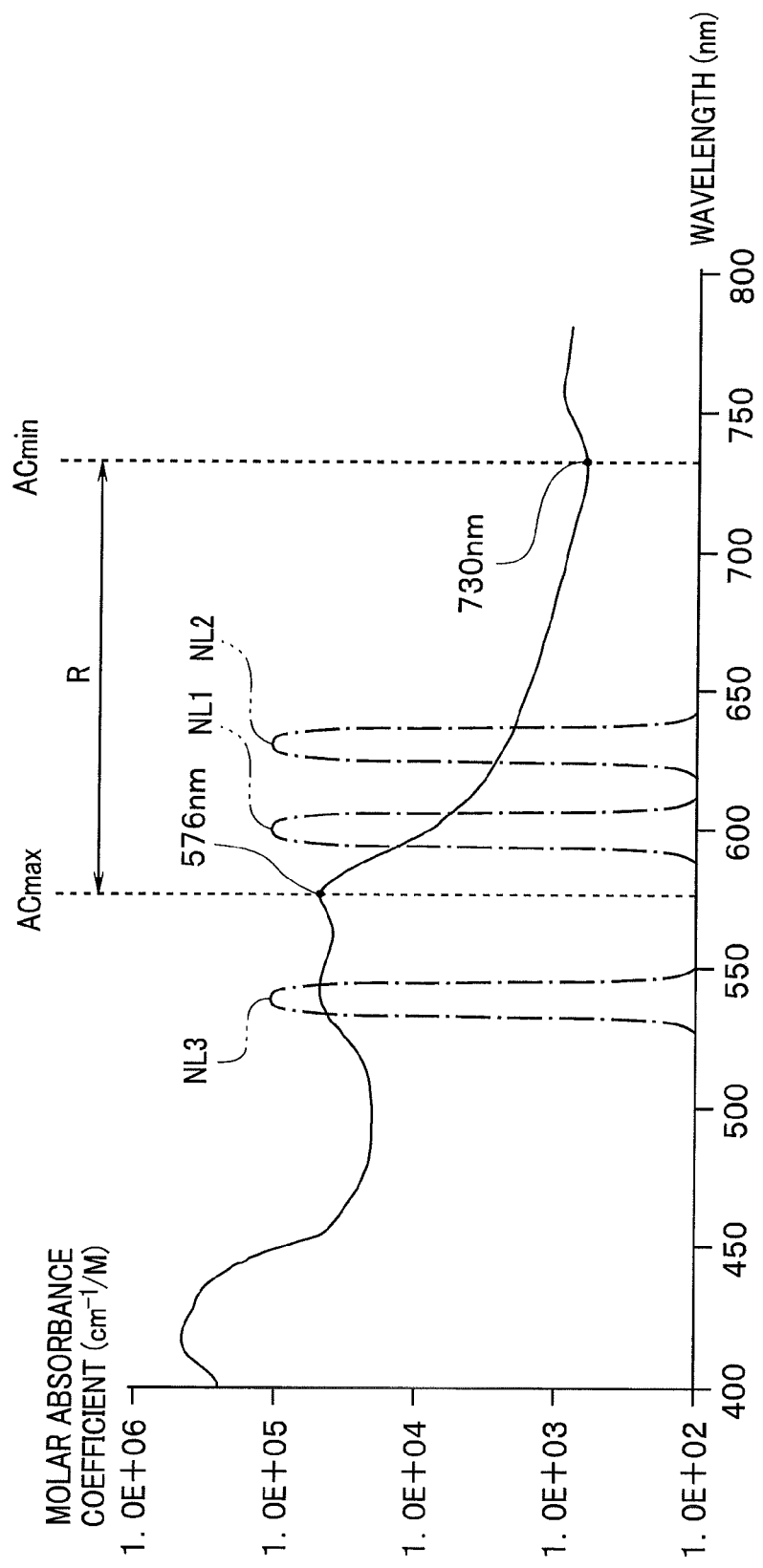
FIG. 4 is a diagram showing a light absorption characteristic of venous blood according to the first embodiment of the present invention.

Here, a light absorption characteristic of venous blood will be described. FIG. 4 is a diagram showing the light absorption characteristic of venous blood. A vertical axis in FIG. 4 indicates a molar absorption coefficient ($cm^{-1}/M$) and a horizontal axis indicates wavelength. Note that, though illumination lights of the three narrowband lights are influenced by a scattering characteristic of living tissue itself, the scattering characteristic of the living tissue itself decreases almost monotonously relative to increase in wavelength, and, therefore, FIG. 4 will be described as a diagram of the light absorption characteristic of the living tissue.

In general, venous blood includes oxyhemoglobin ($HbO_2$) and reduced hemoglobin (Hb) (hereinafter, generically referred to simply as hemoglobin) at the rate of about 60:40 to 80:20. Light is absorbed by hemoglobin, but the absorption coefficient differs according to light wavelength. FIG. 4 shows the light absorption characteristic of venous blood for each wavelength from 400 nm to about 800 nm, and, within a range from 550 nm to 750 nm, the absorption coefficient shows a maximum value at a point of a wavelength of about 576 nm, and a minimum value at a point of a wavelength of about 730 nm.

In the narrowband light observation mode, three narrowband lights are radiated, and each return light is received by the CCD 2.

A narrowband light near the wavelength of 600 nm (hereinafter referred to as a first narrowband light NL1) is a light of a wavelength band within a wavelength band R from a maximum value ACmax of the absorption characteristic of hemoglobin (here, an absorption coefficient at the wavelength of 576 nm) to a minimum value ACmin (here, an absorption coefficient at the wavelength of 730 nm).

A narrowband light near the wavelength of 630 nm (hereinafter referred to as a second narrowband light NL2) is also a light within the wavelength band R from the maximum value ACmax of the absorption characteristic of hemoglobin to the minimum value ACmin. However, it is a light of a wavelength band longer than the wavelength of the first narrowband light NL1 with a lower absorption coefficient in which the scattering characteristic of living tissue is suppressed. That the scattering characteristic is suppressed means that the scattering coefficient decreases toward the long wavelength side.

That is, the light source device 4 radiates the first illumination light NL1 having a peak wavelength of spectral characteristic between a wavelength band that includes the maximum value ACmax and a wavelength band at the minimum value ACmin in the absorption characteristic of living tissue.

Furthermore, here, the light source device 4 also radiates a second illumination light NL2 having a lower value of the absorption characteristic than the image signal P1 by the first illumination light NL1 and having a peak wavelength of such a spectral characteristic that the scattering characteristic of living tissue is suppressed.

Furthermore, the light source device 4 also radiates a narrowband light near the wavelength of 540 nm (hereinafter referred to as a third narrowband light NL3). The third narrowband light NL3 is a light of a wavelength band outside the wavelength band R from the maximum value ACmax to minimum value ACmin of the absorption characteristic of hemoglobin, which is an illumination light which can be transmitted by a predetermined distance from an epithelium of a mucosal surface of a subject.

The CCD 2 outputs an image pickup signal of each of images of the three narrowband lights. Therefore, each image includes multiple pixel signals based on each of return lights of the first, second and third narrowband lights NL1, NL2 and NL3.

Figure 5:
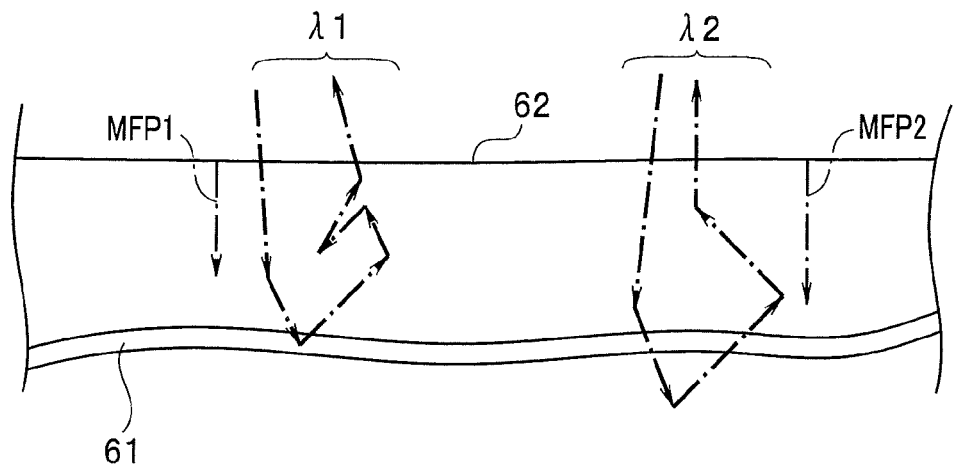
FIG. 5 is a diagram for illustrating light propagation volume in living tissue, of a first narrowband light NL1 ($\lambda 1$) and a second narrowband light NL2 ($\lambda 2$) according to the first embodiment of the present invention.

Furthermore, light propagation in living tissue of the first and second narrowband lights NL1 and NL2 which are illumination lights will be described. FIG. 5 is a diagram for illustrating light propagation volume in living tissue of the first narrowband light NL1 (λ1) and the second narrowband light NL2 (λ2). Each of the first and second narrowband lights NL1 and NL2 repeats multiple scattering processes in living tissue, and, as a result, emitted from a mucosal surface as return lights. The first and second narrowband light NL1 and NL2 have mean free paths MFP1 and MFP2, respectively. The mean free path MFP1 of the first narrowband light NL1 is shorter than the mean free path MFP2 of the second narrowband light NL2.

As shown in FIG. 5, the first narrowband light NL1 near the wavelength of 600 nm (λ1) reaches the vicinity of the blood vessel 61, and the second narrowband light NL2 near the wavelength 630 nm (λ2) reaches a position slightly deeper than the blood vessel 61. Therefore, by using this first narrowband light NL1, it becomes possible to display a relatively thick blood vessel with a diameter of 1 to 2 mm existing in a relatively deep part 1 to 2 mm under a living mucosal epithelium.

Furthermore, as described later, a thicker blood vessel in a deeper part can be displayed by the second narrowband light NL2 near the wavelength of 630 nm (λ2).

Here, description will be made on a theoretical basis for the face that, by using this first narrowband light NL1 near the wavelength of 600 nm (λ1), it becomes possible to display a relatively thick blood vessel existing in a relatively deep part under a living mucosal epithelium with high contrast.

Figure 6:
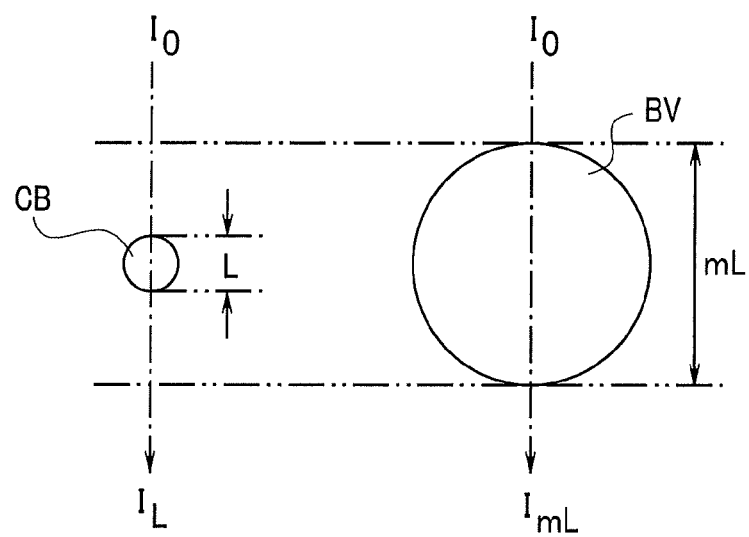
FIG. 6 is a diagram for illustrating a theoretical basis for a fact that a relatively thick blood vessel existing in a relatively deep part under a living mucosal epithelium can be displayed, according to the first embodiment of the present invention.

FIG. 6 is a diagram for illustrating a theoretical basis for the fact that it becomes possible to display a relatively thick blood vessel existing in a relatively deep part under a living mucosal epithelium. In FIG. 6, a relatively thick blood vessel is denoted by BV, and a capillary vessel is denoted by CB.

Here, a simplified model is assumed in which a return light for an incident light is assumed to be a transmitted light for the incident light, and such a wavelength is determined that the amount of light of the return light is maximized for the capillary vessel.

As shown in FIG. 6, when the capillary vessel CB is a medium, a transmittance which is a ratio of output light intensity $I_L$ to input light intensity $I_O$ of a light inputted to the capillary vessel CB is shown by a following equation (1) from the Beer-Lambert law:

$$\frac{I_L}{I_O} = \exp(-\mu L) \quad \text{Equation (1)}$$

Here, L[m] indicates a propagation distance (meter), which is a diameter of the capillary vessel CB; L>0 is satisfied; $\mu[m^{-1}]$ is a coefficient of absorption per unit meter; and $\mu$>0 is satisfied.

Similarly, as shown in FIG. 6, a transmittance, which is a ratio of output light intensity $I_{mL}$ to input light intensity $I_O$ inputted to the blood vessel BV with a diameter mL, is shown by a following equation (2):

$$\frac{I_{mL}}{I_O} = \exp(-\mu mL) \quad \text{Equation (2)}$$

Here, as for m, m>1 is satisfied, and mL[m] indicates a propagation distance (meter) which is a diameter of the blood vessel BV.

A difference $f(\mu)$ between a transmittance for the propagation distance L and a transmittance for the propagation distance mL is indicated by a following equation (3) from the above equations (1) and (2).

$$f(\mu) = \frac{I_L}{I_O} - \frac{I_{mL}}{I_O} = \exp(-\mu L) - \exp(-\mu mL) \quad \text{Equation (3)}$$

The difference $f(\mu)$ between the transmittances always takes a positive value. By differentiating both sides of this equation (3) with $\mu$, the equation (3) is arranged like a following equation (4):

$$\frac{df}{d\mu} = -L\exp(-\mu L) + mL\exp(-\mu mL) \quad \text{Equation (4)}$$
$$= L\{m\exp(-\mu mL) - \exp(-\mu L)\}$$

It is when the condition of a following equation (5) is satisfied that the right side of the equation (4) becomes 0. After transition from the equation (5) to an equation (6), the condition is indicated by an equation (7).

$$\exp(-\mu L) = m\exp(-\mu mL) \quad \text{Equation (5)}$$

$$-\mu L = \ln(m) - \mu mL \quad \text{Equation (6)}$$

$$\mu = \frac{\ln(m)}{(m-1)L} \quad \text{Equation (7)}$$

When the value of μ shown in the equation (7) is taken, f takes a maximum value, that is, the contrast of the blood vessel BV shows a maximum value.

Here, when the equation (7) is substituted into the equation (3), the maximum value $f_{max}$ of f becomes a value shown by a following equation (8).

$$f_{max} = \exp\left\{-\frac{\ln(m)}{m-1}\right\} - \exp\left\{-\frac{m\ln(m)}{m-1}\right\} \quad \text{Equation (8)}$$

Figure 7:
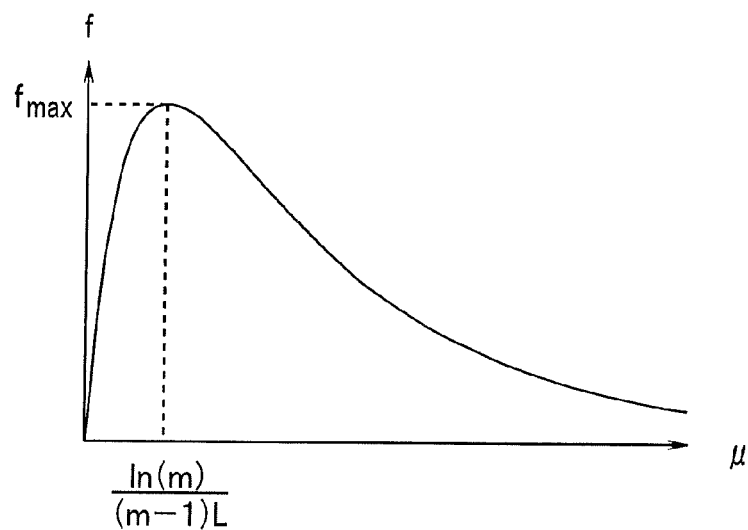
FIG. 7 is a graph showing a function of f according to the first embodiment of the present invention.

FIG. 7 is a graph showing a function of f. As shown in FIG. 7, it is necessary to select the absorption coefficient μ in the equation (7) in order to maximize the transmittances of two transmitted lights with different optical path differences. When $\mu_a[m^{-1}M^{-1}]$ indicates an absorption coefficient per mol, and c[M] indicates concentration (mol) (a mol absorption coefficient) of an absorbing substance, the equation (1) is indicated by a following equation (9).

$$\mu = c\mu_a \quad \text{Equation (9)}$$

The absorption coefficient per mol $\mu_a=[m^{-1}M^{-1}]$ is indicated by a following equation (10), from the equations (7) and (9). In this case, f takes the maximum value $f_{max}$.

$$\mu_a = \frac{\ln(m)}{(m-1)cL} \quad \text{Equation (10)}$$

For example, when two kinds of blood vessels, such as a capillary vessel CB that L is 0.1 mm (that is, the diameter is 0.1 mm) and such a thick blood vessel BV that m is 10 (that is, the diameter is 1 mm), are assumed, c is estimated to be about $2.0 \times 10^{-3}$ [M] from a standard value of hemoglobin concentration. Note that it is assumed that a standard value of male hemoglobin concentration is 12.4 to 17.0 g/dl, and molality of hemoglobin is $6.6 \times 10^4$ g/mol.

When this value is substituted into the equation (10), the absorption coefficient $\mu_a[m^{-1}M^{-1}]$ is as indicated by a following equation (11).

$$\mu_a \approx \frac{\ln(10)}{(10-1) \times 2 \times 10^{-3} \times 10^{-4}} = 1.3 \times 10^6 [m^{-1}m^{-1}] \quad \text{Equation (11)}$$
$$= 1.3 \times 10^4 (cm^{-1}m^{-1})$$

In FIG. 4, such a wavelength that a value of the vertical axis becomes the value of the equation (11) is about 600 nm That is, by using the first narrowband light NL1 with the wavelength of 600 nm (λ1), it becomes possible to display a relatively thick blood vessel existing in a relatively deep part under a living mucosal epithelium with high contrast.

Figure 8:
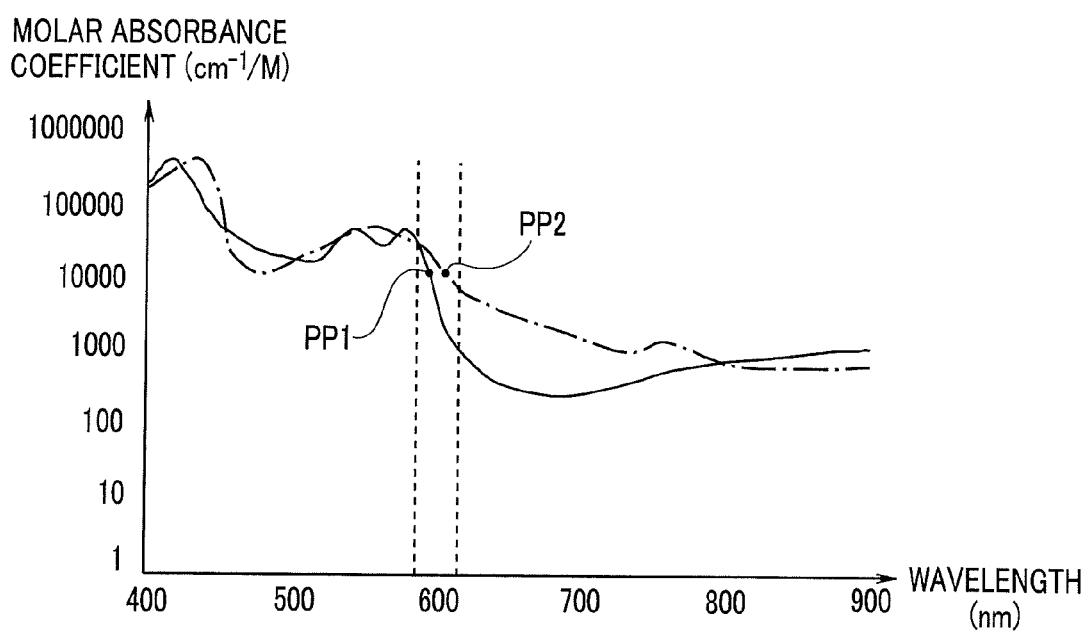
FIG. 8 is a diagram showing the light absorption characteristic of oxyhemoglobin ($HbO_2$) and reduced hemoglobin (Hb) according to the first embodiment of the present invention.

As described above, the wavelength band of the first narrowband light NL1 is a wavelength band where difference between light transmittances of a capillary vessel under a living mucosa of a subject and a blood vessel having a diameter longer than that of the capillary vessel is a predetermined value or more. FIG. 8 is a diagram showing the light absorption characteristics of oxyhemoglobin ($HbO_2$) and reduced hemoglobin (Hb). In FIG. 8, a solid line graph indicates the absorption characteristic of oxyhemoglobin ($HbO_2$), and a dashed-dotted line graph indicates the absorption characteristic of reduced hemoglobin (Hb). From FIG. 8, it is seen that the wavelength satisfying the above equation (11) is about 590 nm indicated by a point of PP1 in the case of oxyhemoglobin ($HbO_2$) and about 602 nm indicated by a point of PP2 in the case of reduced hemoglobin (Hb). Note that it is necessary to pay attention to the fact that, though an optical path length corresponds to thickness of a blood vessel when there is not light scattering, an optical path length does not correspond to thickness of a blood vessel when light scattering cannot be ignored.

There is variation in diameters of the blood vessel BV in a deep part and the capillary vessel CB in an epithelium. Therefore, calculation similar to the above has been performed for a case where each of the diameters of the blood vessel BV in a deep part and the capillary vessel CB in an epithelium are changed.

FIG. 9 is a table showing a result of calculation for combinations between cases where diameter of the capillary vessel CB is 0.01 mm and 0.1 mm and cases where diameter of the thick blood vessel BV is 1 mm and 2 mm From FIG. 9, it is seen that the wavelength satisfying the equation (11) is, as an average value, about 590 nm in the case of oxyhemoglobin ($HbO_2$) and about 603 nm in the case of reduced hemoglobin (Hb).

A minimum wavelength in FIG. 9 is 586 nm, and a maximum wavelength is 614 nm Therefore, from FIG. 9, a range of light in which a relatively thick blood vessel can be displayed with high contrast is from 585 nm, which is the minimum wavelength, to 615 nm, which is the maximum wavelength. That is, by using a narrowband light within a range from 15 nm before and 15 nm after the wavelength of 600 nm, within a range indicated by dotted lines in FIG. 8, a relatively thick blood vessel can be displayed with high contrast.

Figure 27:
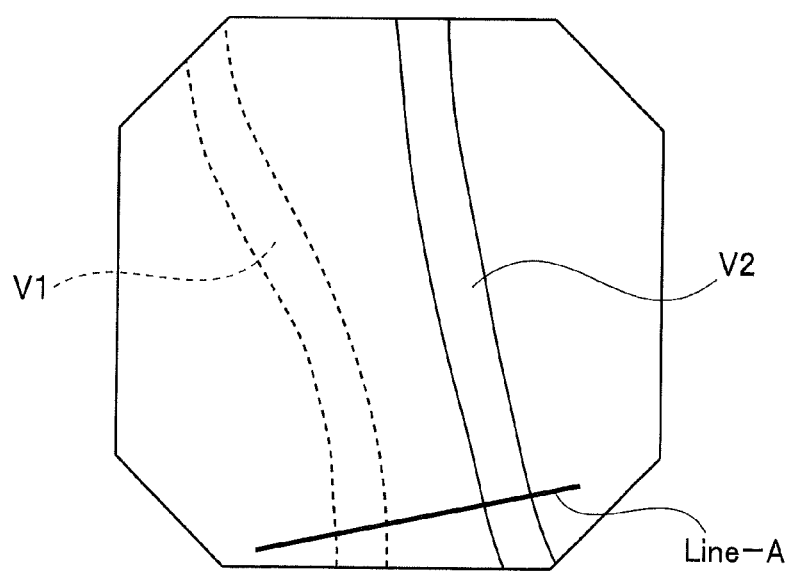
FIG. 27 is a schematic diagram of an image obtained by photographing an inside of an abdominal cavity of an animal using a spectral endoscope apparatus capable of radiating a narrowband illumination light chronologically at intervals of 10 nm of center wavelength.

FIG. 27 is a schematic diagram of an image obtained by photographing an inside of an abdominal cavity of an animal using a spectral endoscope apparatus capable of radiating a narrowband illumination light chronologically at intervals of 10 nm of center wavelength. More specifically, FIG. 27 shows an image in which monochrome images of 540 nm, 600 nm and 630 nm are allocated to a B channel, a G channel and an R channel, respectively. A blood vessel V1 and a blood vessel V2 in the image are thick blood vessels running from an upper left direction to a lower right direction in the image. The blood vessel V1 is positioned deeper from a mucosal surface than the blood vessel V2. Here, monochrome images of a total of fifteen patterns have been photographed at 10 nm-step intervals from 540 nm over to 680 nm.

Figure 28:
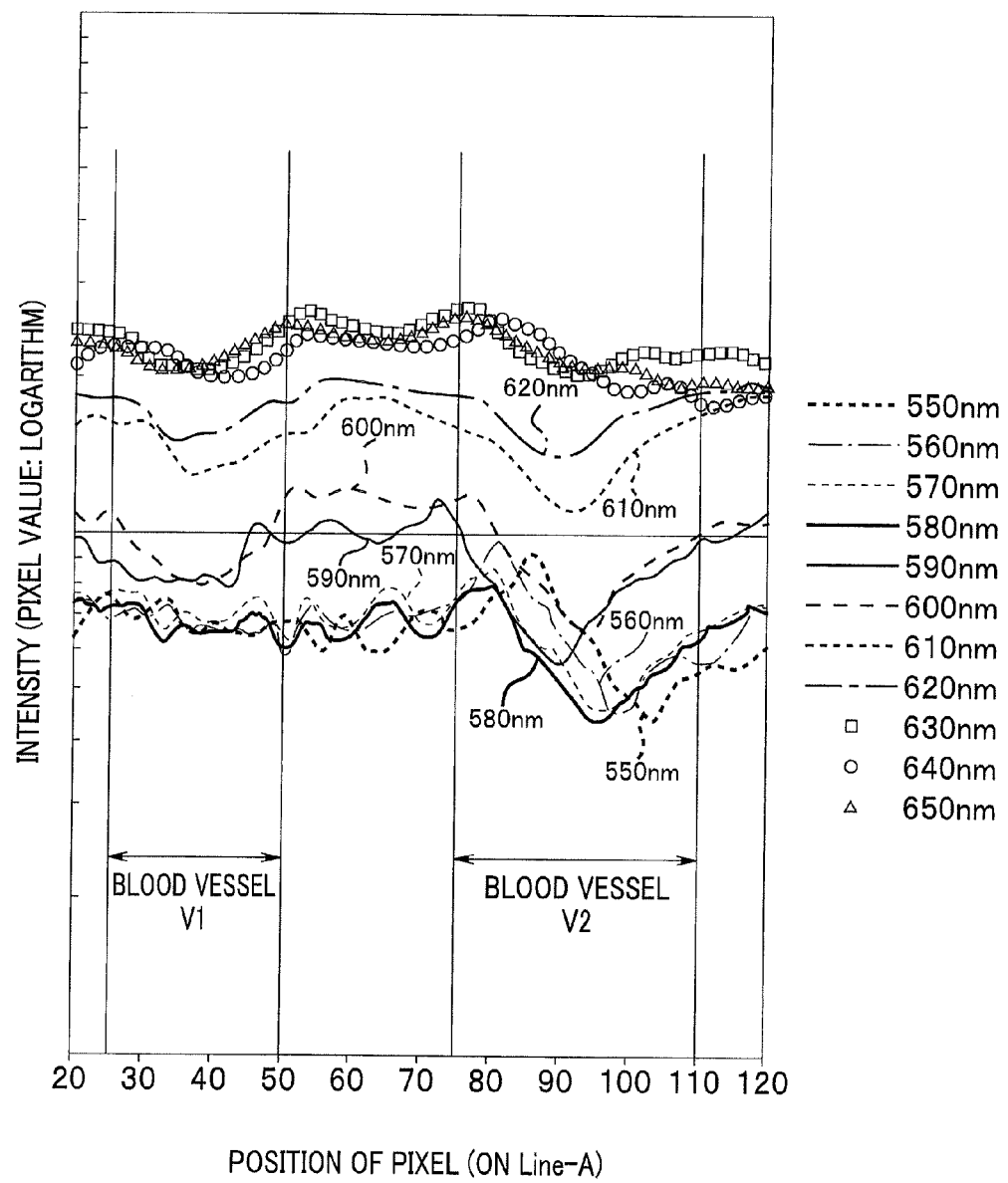
FIG. 28 is a graph showing, for multiple monochrome images shown in FIG. 27, intensities (logarithmically displayed pixel values) on Line-A in each image are shown on a vertical axis.

FIG. 28 is a graph showing, for the multiple monochrome images shown in FIG. 27, intensities (logarithmically displayed pixel values) on Line-A in each image are shown on a vertical axis. A horizontal axis in FIG. 28 indicates positions of pixels on Line-A in each image. Positions of pixels of the blood vessel V1 are near 25 to 50, and positions of pixels of the blood vessel V2 are near 75 to 110. It is seen from FIG. 28 that an illumination wavelength the intensity of which decreases in both of the blood vessel V2 existing in a relatively shallow part and the blood vessel V1 positioned in a deep part, that is, a wavelength in which an illumination light is strongly absorbed in the blood vessels V1 and V2 is about 590 to 620 nm.

Therefore, in order to detect a blood vessel existing from a relatively shallow part to a deep part, an about 590 to 620 nm narrowband light is important wavelength information. The blood vessel V1 exists in a part about 1 to 2 mm deep from a mucosal surface. Note that a result of this experiment almost corresponds to a result of the theoretical calculation by the Beer-Lambert law described before (a relatively thick blood vessel can be displayed with high contrast by using a narrowband light within a range from 15 nm before and 15 nm after the wavelength of 600 nm).

As described above, the illumination means or the illumination section that includes the light source device 4 to display a thick blood vessel in a relatively deep part from a living mucosal epithelium with good contrast radiates the narrowband light NL1 which is an illumination light having a peak wavelength of spectral characteristic between a wavelength band including the maximum value ACmax and a wavelength band at the minimum value ACmin in the absorption characteristic of living tissue.

Note that, though an image signal of a narrowband light near the wavelength of 600 nm is generated here, it is possible to display a blood vessel in a deep mucosa by generating an image signal having a predetermined wavelength width and having a peak wavelength of spectral characteristic between a wavelength band which includes a maximum value and a wavelength band at a minimum value in the absorption characteristic of living tissue as shown in FIG. 4 because there is variation among diameters of blood vessels and there are various depths as described above.

Furthermore, the light source device 4 also radiates the narrowband light NL2 having a lower value in the absorption characteristic of a return light by the first narrowband light NL1, having a peak wavelength of spectral characteristic in which a scattering characteristic of living tissue is suppressed, and being an illumination light of a wavelength band different from the wavelength band of the first narrowband light NL1, and the third narrowband light NL3 that can be transmitted by a predetermined distance from a subject's epithelium.

The narrowband light NL2 is a narrowband light for obtaining an image of a blood vessel in a deeper part than a blood vessel displayed with the narrowband light NL1, and the third narrowband light NL3 is a narrowband light for obtaining an image of a capillary vessel in an epithelium.

Figure 10:
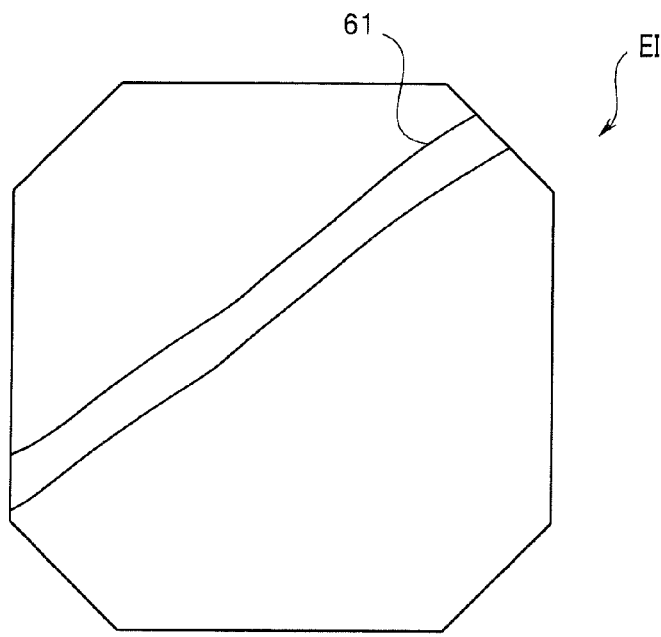
FIG. 10 is a diagram showing an example of an endoscopic image for illustrating a display example of a blood vessel in an endoscopic image in a narrowband light observation mode according to the first embodiment of the present invention.

Next, processing in the image processing section 101 will be described. FIG. 10 is a diagram showing an example of an endoscopic image for illustrating a display example of a blood vessel in an endoscopic image in the narrowband light observation mode.

In the normal light observation mode, in a picked-up endoscopic image EI, a blood vessel in a deep part 1 to 2 mm from an epithelium is not displayed or is difficult to be displayed on the endoscopic image EI on the observation monitor 5.

In comparison, in the narrowband light observation mode, when a deep-part blood vessel exists in the picked-up endoscopic image EI, the blood vessel 61 is displayed on the endoscopic image EI as shown in FIG. 10.

Thus, the image processing section 101 constitutes image output means or an image output section for, after image pickup by the image pickup means or the image pickup section, outputting an image signal P1 (λ1) of a predetermined wavelength band having a peak wavelength of spectral characteristic between a wavelength band including the maximum value ACmax and a wavelength band at the minimum value ACmin in the absorption characteristic of living tissue.

According to an experiment performed by the applicant, when an image is generated with the use of the narrowband light NL1 as described above, it is possible not only to display a relatively thick blood vessel in a deep mucosa but also to display a state of a flow of bleeding in a state that a mucosal surface is covered with blood due to the bleeding from a mucosa.

Conventionally, in white color light observation, when a mucosal surface is covered with blood, a place where bleeding occurs, that is, a bleeding point cannot be seen, and, therefore, the surgeon cannot perform treatment to stop the bleeding quickly. In comparison, according to the present embodiment, since it becomes easier to find the bleeding point on the mucosal surface under the blood, the surgeon can perform hemostasis treatment quickly.

Figure 11:
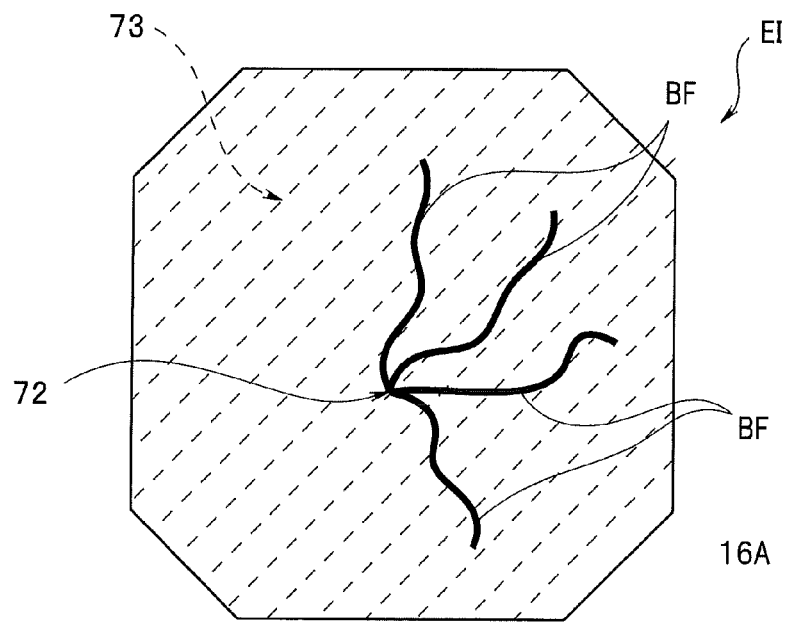
FIG. 11 is a diagram for illustrating an example of an image obtained by picking up an image of a state of bleeding with a mucosal surface covered with blood in the narrowband light observation mode, according to the first embodiment of the present invention.
Figure 12:
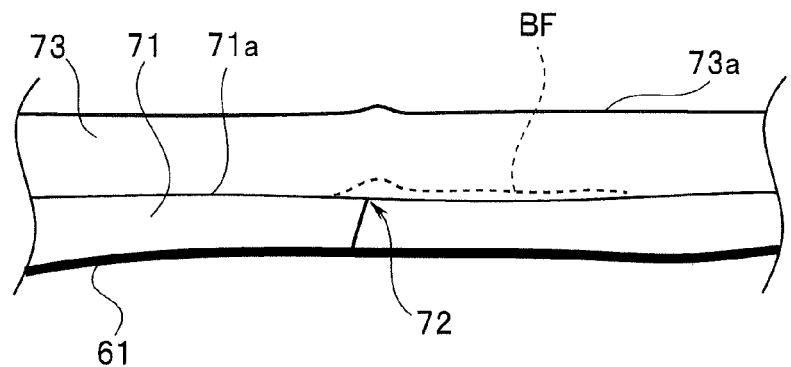
FIG. 12 is a diagram for illustrating the state of bleeding with a mucosal surface covered with blood according to the first embodiment of the present invention.

FIG. 11 is a diagram for illustrating an example of an image obtained by picking up an image of a state of bleeding with a mucosa covered with blood in the narrowband light observation mode. FIG. 12 is a diagram for illustrating the state of bleeding with a mucosal surface covered with blood.

As shown in FIG. 11, there may be a case where a mucosal surface 71a is covered with blood 73 (indicated by dotted lines) of bleeding from a bleeding point 72 on the mucosal surface 71a of a mucosa 71. When the blood 73 is observed in the narrowband light observation mode described above, a narrowband light near the wavelength of 600 nm is transmitted through the blood 73, and blood flowing from the bleeding point 72 on the mucosal surface 71a is displayed, as shown in FIG. 11. This is because density (that is, concentration) of blood spouting from the bleeding point 72 is high in the vicinity of the bleeding point 72. Therefore, it is possible to visually confirm a flow of blood BF flowing from the bleeding point 72 and, therefore, identify the bleeding point 72 under the blood 73, and the surgeon can quickly perform hemostasis treatment for the bleeding point 72, which leads to shortening of an operation time period.

Figure 13:
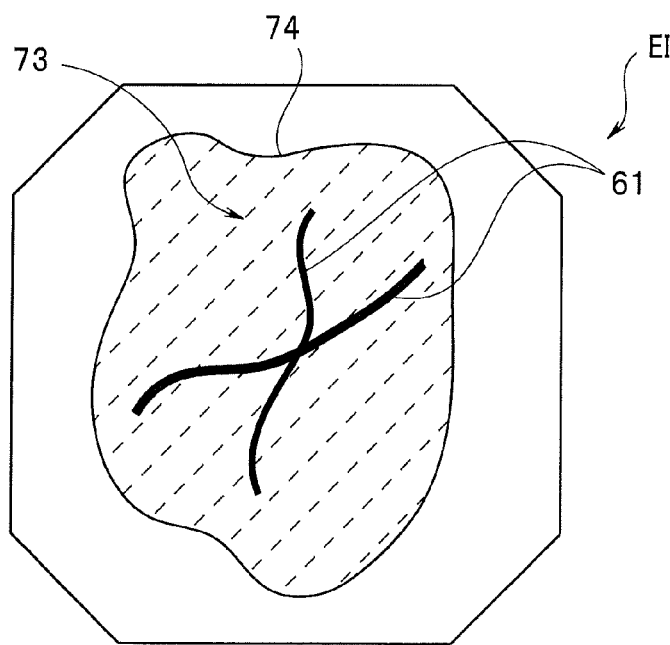
FIG. 13 is a diagram for illustrating an example of an image obtained by picking up an image of a blood puddle portion on a mucosal surface in the narrowband light observation mode, according to the first embodiment of the present invention.

Furthermore, when an image is generated with the use of the narrowband light NL1 as described above, it is possible to display a blood vessel under a mucosa even if there is a blood puddle in a body. FIG. 13 is a diagram for illustrating an example of an image obtained by picking up an image of a blood puddle portion on a mucosal surface in the narrowband light observation mode. The blood puddle portion in the body is made of mixture of bleeding and water caused by treatment. In the white color light observation, such a blood puddle portion is observed only in red color of the blood.

When a blood puddle portion 74 is observed in the narrowband light observation mode described above, a narrowband light near the wavelength of 600 nm is transmitted through the blood 73 that includes the water of the blood puddle portion, and the blood vessel 61 under the mucosal surface 71a is displayed as shown in FIG. 13.

Therefore, when the mode is switched to the narrowband light observation mode during an operation, the blood vessel 61 under the mucosal surface under the blood puddle portion can be seen on the observation monitor.

Next, processing by the image processing section 101 will be described. The image processing section 101 has the color conversion processing section 101b to execute color conversion processing.

(Color Conversion Processing by Image Processing Section)

Next, processing in the color conversion processing section 101b will be described. A first image signal P1 (λ1), a second image signal P2 (λ2) and a third image signal P3 (λ3) are inputted to the color conversion processing section 101b.

Figure 14:
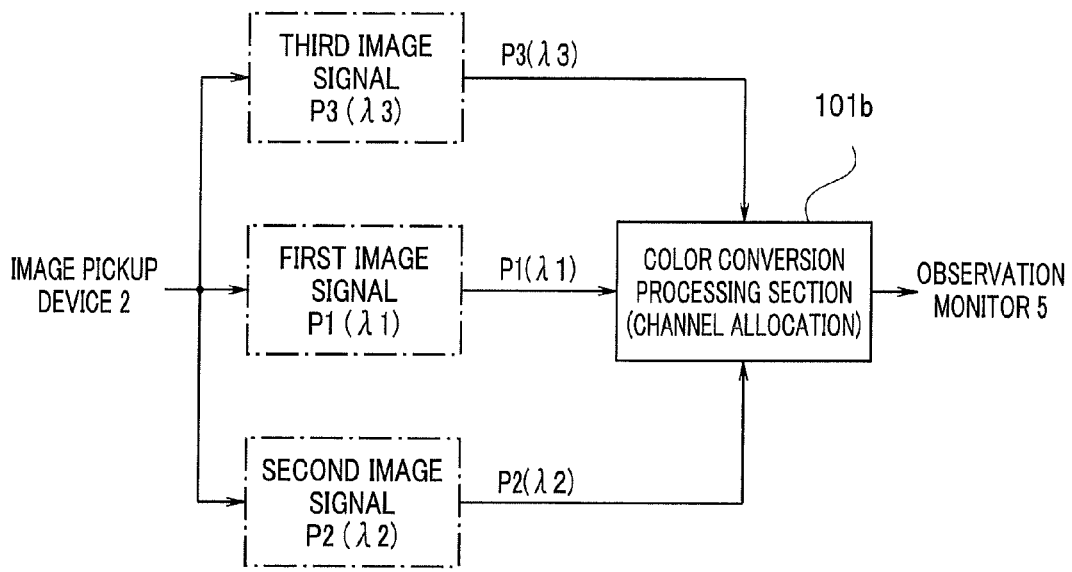
FIG. 14 is a block diagram for illustrating a configuration of an image processing section 101 according to the first embodiment of the present invention.

FIG. 14 is a block diagram for illustrating a configuration of the image processing section 101. Three image signals from the image pickup device are inputted to the color conversion processing section 101b. The color conversion processing section 101b performs color conversion processing by allocation of channels for the first image signal P1 (λ1), the second image signal P2 (λ2) and the third image signal P3 (λ3) and outputs the signals to the observation monitor 5. In order to display the blood vessel 61 in a deep part with high contrast by the narrowband light NL1 near the wavelength of 600 nm, the color conversion processing section 101b allocates the first image signal P1 (λ1) to three channels of BGR to output the first image signal P1 (λ1) to the observation monitor 5 as a monochrome image. Note that, if there is a monochrome image display circuit, the first image signal P1 (λ1) may be inputted to the monochrome image display circuit to output the first image signal P1 (λ1) to the observation monitor 5 as a monochrome image.

As a result, the blood vessel 61 shown in FIG. 10 is monochromatically displayed on the endoscopic image EI with high contrast in the narrowband light observation mode. The blood flow BF in FIG. 11 and the blood vessel under the blood puddle in FIG. 13 are also monochromatically displayed with high contrast.

Thus, the image processing section 101 constitutes image output means or an image output section for outputting the first image signal P1 (λ1) on the basis of an image signal obtained by picking up an image of a return light by the CCD 2 which is the image pickup means or the image pickup section.

Note that the color conversion processing section 101b may perform color conversion processing using at least one of the second image signal P2 (λ2) and the third image signal P3 (λ3) in addition to the first image signal P1 (λ1). First to third modifications of the color conversion processing by the color conversion processing section 101b will be described below.

First, the first modification will be described.

The color conversion processing section 101b of the first modification performs processing of allocating the first image signal P1 (λ1), the second image signal P2 (λ2) and the third image signal P3 (λ3) to the channels of G, R and B, respectively.

Here, for example, the color conversion processing section 101b performs processing of a following equation (12), and a luminance value ImA (λ1) of the first image signal P1 (λ1), a luminance value Im (λ2) of the second image signal P2 (λ2) and a luminance value Im (λ3) of the third image signal P3 (λ3) are allocated to the G, R and B channels, respectively.

$$\begin{pmatrix} B \\ G \\ R \end{pmatrix} = \begin{pmatrix} 1 & 0 & 0 \\ 0 & 1 & 0 \\ 0 & 0 & 1 \end{pmatrix} \begin{pmatrix} Im(\lambda 3) \\ ImA(\lambda 1) \\ Im(\lambda 2) \end{pmatrix} \quad \text{Equation (12)}$$

According to the equation (12), the relatively thick blood vessel 61 in a deep part is displayed in rather reddish color and is easy for the surgeon to identify.

Figure 15:
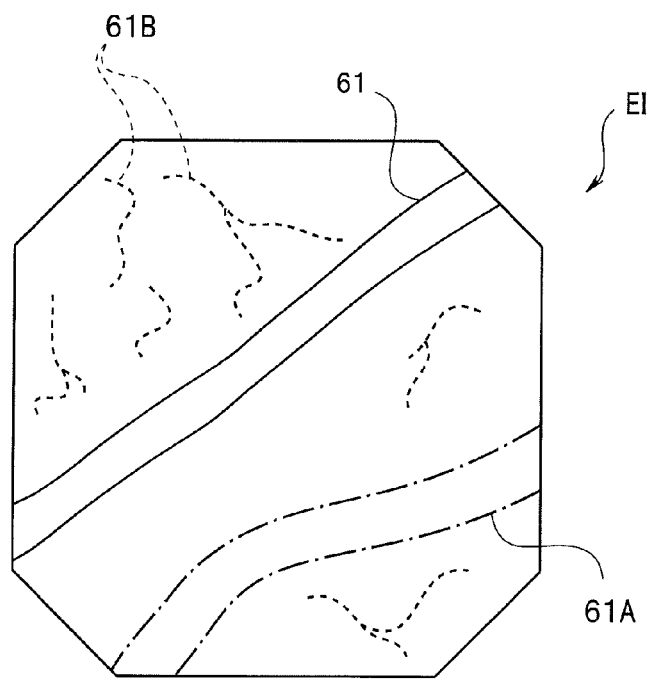
FIG. 15 is a diagram for illustrating a display example of an endoscopic image using three image signals according to the first embodiment of the present invention.

FIG. 15 is a diagram for illustrating a display example of an endoscopic image using the three image signals. The blood vessel 61 in a deep part indicated by solid lines is displayed in rather reddish color; a blood vessel 61A (indicated by dashed-dotted lines) in a deeper part than the blood vessel 61 is displayed in color from blue to black; and capillary vessels 61B indicated by broken lines is displayed in almost yellow. Especially, a mucosa of living tissue and, further, blood on a mucosal surface are also displayed in almost yellow.

Note that, though the third narrowband light NL3 is a light near the wavelength of 540 nm here, a blue light with a shorter wavelength, for example, a light near a wavelength of 460 nm or 415 nm may be used to obtain epithelium information.

By allocating the narrowband light NL1 near the wavelength of 600 nm with a high degree of absorption to the G channel and the narrowband light NL2 near the wavelength of 630 nm with a degree of absorption lower than that of the narrowband light NL1 to the R channel, each of the blood vessel 61 and the blood vessel 61A can be displayed in color (rather reddish color) different from the color of the epithelium of living tissue.

Even if there is blood due to bleeding on the mucosal surface of living tissue, the blood vessel 61 in a deep part and the blood vessel 61A in a deeper part are displayed in different color and, therefore, they are easy for the surgeon to visually confirm.

When the three image signals are used, the bleeding point 72 described with reference to FIGS. 11 and 12 changes between yellow and orange alternately. This is because density (or concentration) of blood or thickness of a blood layer at the bleeding point 72 dynamically changes during bleeding. At a place far from the bleeding point 72, since the density of blood or the thickness of the blood layer does not dynamically change, the color tone of blood remains yellow or orange.

As described above, when the three image signals are used, color tones in an image change near the bleeding point 72, and, therefore, the surgeon can easily recognize the bleeding point 72 by the change in color tones. The surgeon can also recognize the thickness of the layer of the blood 73 by change between yellow and orange.

When the three image signals are used, an advantage also occurs that not only noticeability of the blood vessels under bleeding described with reference to FIG. 13 but also noticeability of a foreign matter in blood is improved. If light adjustment is performed with an R-channel band signal weighted most heavily, a foreign matter in blood is seen more easily than an image at the time of white light observation in the normal light observation mode because the two narrowband lights near the wavelengths of 600 nm and 630 nm are easily transmitted through blood because of their weak absorption characteristic. Since the two narrowband lights near the wavelengths of 600 nm and 630 nm are easily transmitted not only through blood but also through bile, urine and the like, a foreign matter in or under such liquids is easily seen.

Note that the first image signal P1 (λ1), the second image signal P2 (λ2) and the third image signal P3 (λ3) may be allocated to the G, B and R channels, respectively. In that case, by performing intensity adjustment and the like of each image signal, such as multiplication of each value of the matrix of the equation (12) by a coefficient, a display image similar to an image obtained by the color conversion processing of the above equation (12) can be displayed on the observation monitor 5.

In the color conversion processing section 101b, a following equation (13) may be used instead of the above equation (12).

$$\begin{pmatrix} B \\ G \\ R \end{pmatrix} = \begin{pmatrix} 1 & 0 & 0 \\ 1 & 0 & 0 \\ 0 & 1 & 0 \end{pmatrix} \begin{pmatrix} \mathrm{Im}(\lambda 3) \\ \mathrm{Im}A(\lambda 1) \\ \mathrm{Im}(\lambda 2) \end{pmatrix} \quad \text{Equation (13)}$$

According to the equation (13), since the blood vessel 61 in a deep part is displayed in blue or bluish green as well as the capillary vessels in an epithelium being displayed reddish, the vessels can be easily identified by the surgeon.

Furthermore, note that a following equation (14) may be used instead of the above equation (12) in the color conversion processing section 101b.

$$\begin{pmatrix} B \\ G \\ R \end{pmatrix} = \begin{pmatrix} 1 & 0 & 0 \\ 0.5 & 0.5 & 0 \\ 0 & 1 & 0 \end{pmatrix} \begin{pmatrix} \mathrm{Im}(\lambda 3) \\ \mathrm{Im}A(\lambda 1) \\ \mathrm{Im}(\lambda 2) \end{pmatrix} \quad \text{Equation (14)}$$

Furthermore, note that a following equation (15) may be used instead of the above equation (12) in the color conversion processing section 101b. Here, $\alpha$ takes a numerical value nearly from 1.0 to 1.5, $\beta$ takes a numerical value nearly from 2.0 to 2.6, and $\gamma$ takes a numerical value nearly from 2.5 to 3.3 (for example, $\alpha:\beta:\gamma=0.56:1.00:1.17$). In this case, since color tone of a blood vessel in a deep part is blush green, and color tone of a mucosa is similar to that of normal observation, the surgeon can perform observation without stress. By setting $\alpha$, $\beta$ and $\gamma$ to numerical values nearly from 2.3 to 2.7, nearly from 2.3 to 2.7, and nearly from 1.7 to 2.1, respectively (for example, $\alpha:\beta:\gamma=1.00:1.00:0.76$), it becomes easy to observe blood vessels in an epithelium and a deep part.

$$\begin{pmatrix} B \\ G \\ R \end{pmatrix} = \begin{pmatrix} \alpha & 0 & 0 \\ \beta & 0 & 0 \\ 0 & \gamma & 0 \end{pmatrix} \begin{pmatrix} \mathrm{Im}(\lambda 3) \\ \mathrm{Im}A(\lambda 1) \\ \mathrm{Im}(\lambda 2) \end{pmatrix} \quad \text{Equation (15)}$$

Note that another example of the channel allocation by the color conversion processing section 101b will be described. For example, at the time of giving treatment, the narrowband light near the wavelength of 540 nm, the narrowband light near the wavelength of 630 nm and the narrowband light near the wavelength of 600 nm may be allocated to the B channel, the G channel and the R channel, respectively, instead of the above equation (12).

At the time of giving a diagnosis, the narrowband light near the wavelength of 540 nm can be allocated to the B channel and the G channel, and the narrowband light near the wavelength of 600 nm or the narrowband light near the wavelength of 630 nm can be allocated to the R channel.

Here, color balance adjustment will be described.

For example, in the case of allocating the narrowband light near the wavelength of 540 nm, the narrowband light near the wavelength of 630 nm and the narrowband light near the wavelength of 600 nm to the B channel, the G channel and the R channel, respectively, it is desirable to amplify the signal of the B channel relative to the signal of the R channel. The signal intensity of the narrowband light near the wavelength of 600 nm is not corrected, and the two signals of the signal of the narrowband light near a wavelength of 650 nm allocated to the B channel and the signal of the narrowband light near the wavelength of 630 nm allocated to the R channel are adjusted so that the intensity of the former signal is 0.7 to 2.5 times as high as the intensity of the latter signal. Note that the color conversion processing may be performed after performing the color balance adjustment, or the color balance processing may be performed after the color conversion processing.

Thereby, color tone difference among a mucosa, fibrous tissue in a white color tone, bleeding in yellow, a carbonized area in black, and a thick blood vessel in color tones from red to magenta becomes more remarkable, and it is possible to obtain a display image from which the surgeon can give treatment or diagnosis more easily.

A color balance adjustment circuit for such color balance adjustment may be provided for a previous stage of the W. B 25 in FIG. 1. In that case, when intensities of illumination lights of the narrowband light near the wavelength of 540 nm and the narrowband light near the wavelength of 630 nm are almost equal to each other, the color balance adjustment circuit sets the signal of the narrowband light near the wavelength of 540 nm allocated to the B channel to be about 0.7 to 1.5 times, and the signal of the narrowband light near the wavelength of 630 nm to be about 0.6 to 1.0 times.

Note that the color balance adjustment may be performed by the color conversion processing section 101b, or may be performed by the light source device 4 adjusting the intensities of the illumination lights, or may be performed by adjusting transmittance of each color of the color filters of the image pickup device.

Next, a second modification will be described. Here, gain adjustment for color balance adjustment is not performed unless otherwise stated. That is, each gain is assumed to be 1.

In the second modification, channels are allocated to two image signals among the three image signals.

As an example, the color conversion processing section 101b of the second modification may perform processing of allocating a first image signal P1 ($\lambda$1) to the G and B channels, and a second image signal P2 ($\lambda$2) to the R channel.

In such allocation, in the endoscopic image EI, bleeding and a blood vessel in a deep part are displayed in rather reddish color, a mucosa is displayed whitish, and capillary vessels in an epithelium are hardly displayed.

As a third modification, processing of allocating the first image signal P1 ($\lambda$1) to the R channel, and the third image signal P3 ($\lambda$3) to the G and B channels may be performed in the color conversion processing section 101b.

In such allocation, in the endoscopic image EI, bleeding and a mucosa are displayed in rather reddish color, and a blood vessel in a deep part is displayed in greenish color.

In this case, gain adjustment of each channel may be performed. For example, if gains of the G and B channels to which the third image signal P3 ($\lambda$3) is allocated is set to be 1.3 to 1.5 times as much as gain of the R channel to which the first image signal P1 ($\lambda$1) is allocated, bleeding and a mucosa are displayed in reddish color, and a blood vessel in a deep part is displayed in color from bluish to greenish.

For example, if the gains of the G and B channels to which the third image signal P3 ($\lambda$3) is allocated and the gain of the R channel to which the first image signal P1 ($\lambda$1 ) is allocated are set so that ascending order of gain is B, R and G, then bleeding and a mucosa are displayed in brown, and a blood vessel in a deep part is displayed in color from bluish to greenish.

Furthermore, for example, if the gains of the G and B channels to which the third image signal P3 (λ3) is allocated and the gain of the R channel to which the first image signal P1 (λ1) is allocated are set so that ascending order of gain is B, G and R, then bleeding and a mucosa are displayed in reddish color, and a blood vessels in a deep part is displayed in greenish color.

As described above, according to the embodiment described above, it is possible to realize the endoscope apparatus 1 that displays a relatively thick blood vessel in a deep mucosa using the first image signal P1 among the three image signals from the image pickup device 2.

That is, a narrowband light having an absorption characteristic as described above, between a maximum value and minimum value of the absorption characteristic of living tissue, as shown in FIG. 4 is radiated to a living mucosa, and, by an image of an obtained return light, a relatively thick blood vessel existing in a relatively deep part of the living mucosa is emphasized and displayed on the screen of the observation monitor 5. Therefore, the surgeon can perform desired treatment such as ESD, looking at and confirming the relatively thick blood vessel.

If, using two or three image signals among the first to third image signals P1, P2 and P3, the color conversion processing section 101b allocates channels to the first image signal P1, the second image signal P2 and the third image signal P3 and outputs the image signals to the observation monitor 5, a relatively deep blood vessel, capillary vessels in a mucosal epithelium and the like can be also displayed.

That is, in the endoscope apparatus 1 described above, a blood vessel existing near an epithelium of living mucosa can be displayed with the use of the third narrowband light NL3.

For example, since the third narrowband light NL3 near the wavelength of 540 nm is used, a state of capillary vessels in an epithelium is also displayed on the screen of the observation monitor 5 together with a thick blood vessel. Furthermore, since the second narrowband light NL2 near the wavelength of 630 nm is used, a state of a blood vessel in a deeper part is also displayed on the screen of the observation monitor 5 together.

Thus, the surgeon can use an endoscopic image on the screen of the observation monitor 5 not only for treatment but also for diagnosis of living tissue, for example, diagnosis of existence of cancer or range diagnosis for identifying a range of cancer, and for discrimination diagnosis for judging whether an affected part is benignant or malignant, from a state of capillary vessels, for example, degree of concentration or dispersion of the capillary vessels. Furthermore, it is possible to perform invasive depth diagnosis and the like taking into account of a blood vessel in a deeper part.

Note that, though the light source device 4 described above generates an illumination light of a desired wavelength band using the xenon lamp 11, the rotating filter 14 and the like, in the endoscope apparatus 1, as indicated by dotted lines, the light source device 4 may be configured to include a light emitting section 11A including a light emitting diode group 11a including multiple light emitting diodes (LEDs) that emit desired wavelength, for example, each of wavelengths of RGB corresponding to the first filter group and each of wavelengths near 600 nm and near 630 nm corresponding to the second filter group. In that case, the light emitting section 11A and the light guide 15 constitute an irradiating section that irradiates an subject with illumination light.

For example, in FIG. 1, instead of the xenon lamp 11, the heat ray cut filter 12, the diaphragm device 13, the rotating filter 14 and the like, the light emitting section 11A indicated by a dotted line is provided in the light source device 4. Furthermore, the light source device 4 is provided with a driving circuit 11b for driving each of the light emitting diodes of the light emitting section 11A at predetermined timings according to each mode. The light emitting section 11A having multiple LEDs 11a receives power source from the power supply 10 and is controlled and driven by the driving circuit 11b under a control signal from the control circuit 17.

When the endoscope apparatus 1 is configured with the use of such a light source device, the same advantages as described above can be also obtained.

Note that the light emitting section 11A may employ a laser diode (LD) that emits predetermined multiple narrowband lights.

In the case where the light source device is mounted with any of a xenon light source, an LED and an LD, and the CCD 2 is not a monochrome image pickup device but is provided with RGB color filters or complementary color filters as the wavelength band limiting means or the wavelength band limiting section that transmits the first narrowband light NL1, advantages equal to those described above can be obtained.

The second narrowband light NL2 shown in FIG. 4 may be a light of a longer wavelength band than the minimum value ACmin of the absorption characteristic of hemoglobin (here, an absorption coefficient at the wavelength of 730 nm). That is, as for the wavelength of the second narrowband light NL2, such a wavelength band that the absorption coefficient is lower than the wavelength of the first narrowband light NL1 and the scattering characteristic of living tissue is suppressed, for example, 740 nm, 770 nm, 805 nm, 810 nm, 850 nm, 870 nm, 880 nm, 910 nm, 940 nm, 1020 nm or 1300 nm can be used to obtain advantages equal to those described above (for example, when the narrowband light NL2 is set to any wavelength from 740 nm to 1300 nm, the narrowband light NL1 is set to any wavelength equal to or longer than 576 nm and at least equal to or shorter than 630 nm). Note that the second narrowband light NL2 can be also generated even when any of a xenon light source, an LED and an LD is mounted as a light source device.

As described above, according to the present embodiment described above, it is possible to provide an endoscope apparatus capable of clearly displaying a blood vessel in a deep mucosa without complicated work of medicine administration being performed.

(Second Embodiment)

In the first embodiment, at least one narrowband light that includes the first narrowband light NL1 is actually radiated to living tissue as an illumination light, and the color conversion processing described above is performed for an image of a return light thereof. In the present embodiment, however, the at least one narrowband light is not actually radiated to living tissue. Image information of a return light of each narrowband light is obtained by so-called spectral estimation, and color conversion processing as described above is performed for a spectral image signal of each wavelength obtained by the spectral estimation. That is, though the first narrowband light NL1 is generated by an illumination device having a rotating filter or a light emitting device such as a light emitting diode, and color conversion processing is performed for images of return lights thereof in the first embodiment described above, an image signal corresponding to the first narrowband light NL1 is obtained by spectral estimation processing, and color conversion processing is performed for a spectral estimation image signal obtained by the spectral estimation in the present embodiment.

Figure 16:
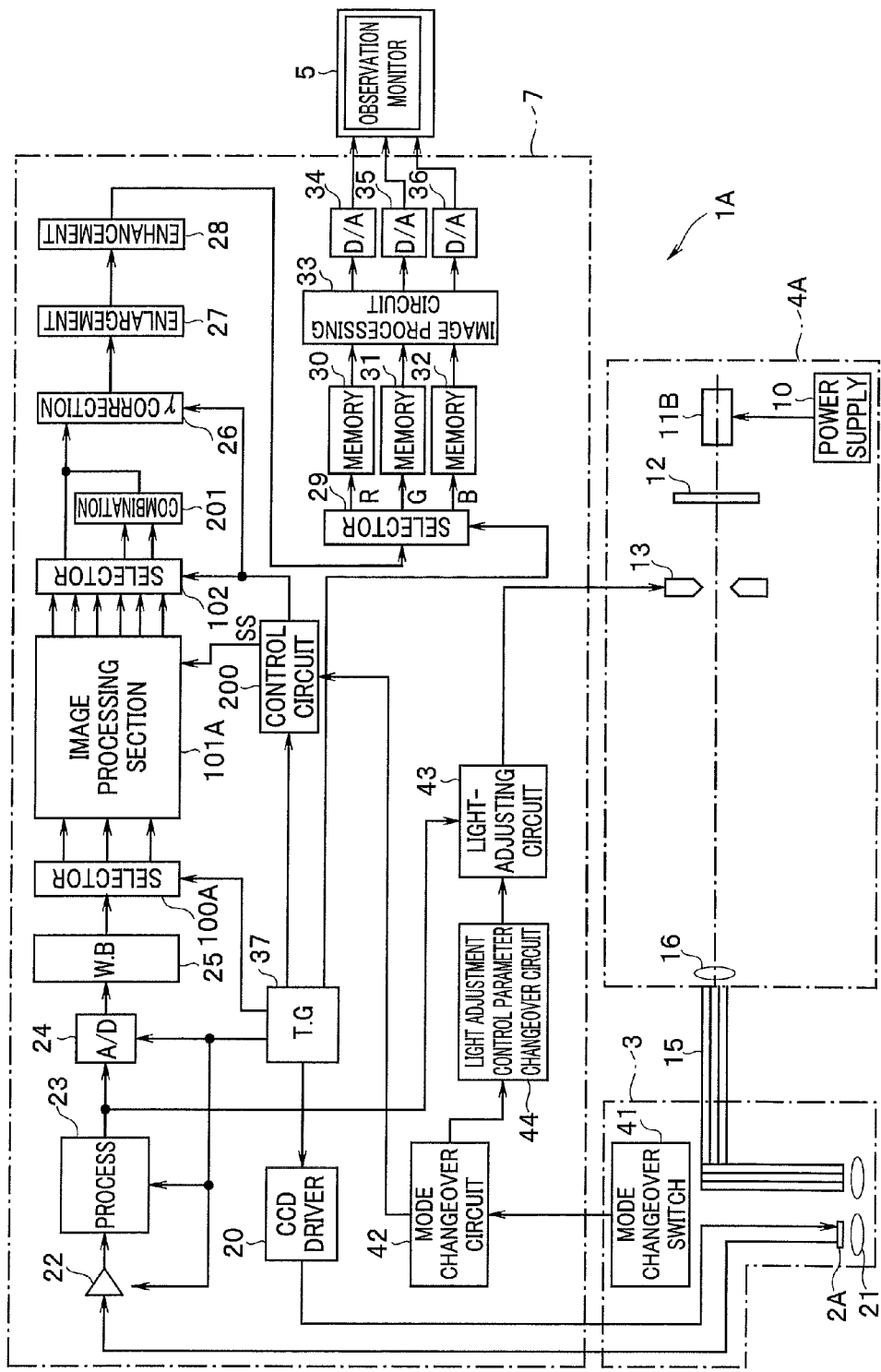
FIG. 16 is a configuration diagram showing a configuration of an endoscope apparatus 1A according to a second embodiment of the present invention.

FIG. 16 is a configuration diagram showing a configuration of an endoscope apparatus 1A according to the second embodiment of the present invention. In FIG. 16, the same components as shown in FIG. 1 are denoted by the same reference numerals and signs and description thereof is omitted. Note that, in FIG. 16 also, a polarizing plate may be arranged on each of a front face of the CCD 2 and a front face of the light guide 15 in a crossed Nichol prism state.

As shown in FIG. 16, a light source device 4A is configured, including a lamp 11B that emits a white light, the heat ray cut filter 12, and the diaphragm device 13. An illumination light from the light source device 4A is radiated to a subject via the light guide 15. Note that the lamp 11B may emit a light other than a white color light.

An image pickup device 2A provided at the distal end of the insertion section of the endoscope 3 is a color image pickup device. The image pickup device 2A is, for example, a color CCD and includes RGB color filters on an image pickup surface. A return light from the subject is received by each pixel section of the image pickup surface via the RGB color filters, which are wavelength band limiting means or wavelength band limiting sections, and image signals of three colors of RGB are outputted from the image pickup device 2A.

A selector 100A outputs the three image signals of RGB to an image processing section 101A. The image processing section 101A has a spectral estimation section, and, in the narrowband light observation mode, outputs a spectral estimation image signal near the wavelength of 600 nm Here, in the narrowband light observation mode, the spectral image estimation section of the image processing section 101A outputs three image signals, more specifically, a spectral estimation image signal near the wavelength of 600 nm, a spectral estimation image signal near the wavelength of 630 nm and a spectral estimation image signal near the wavelength of 540 nm.

Figure 17:
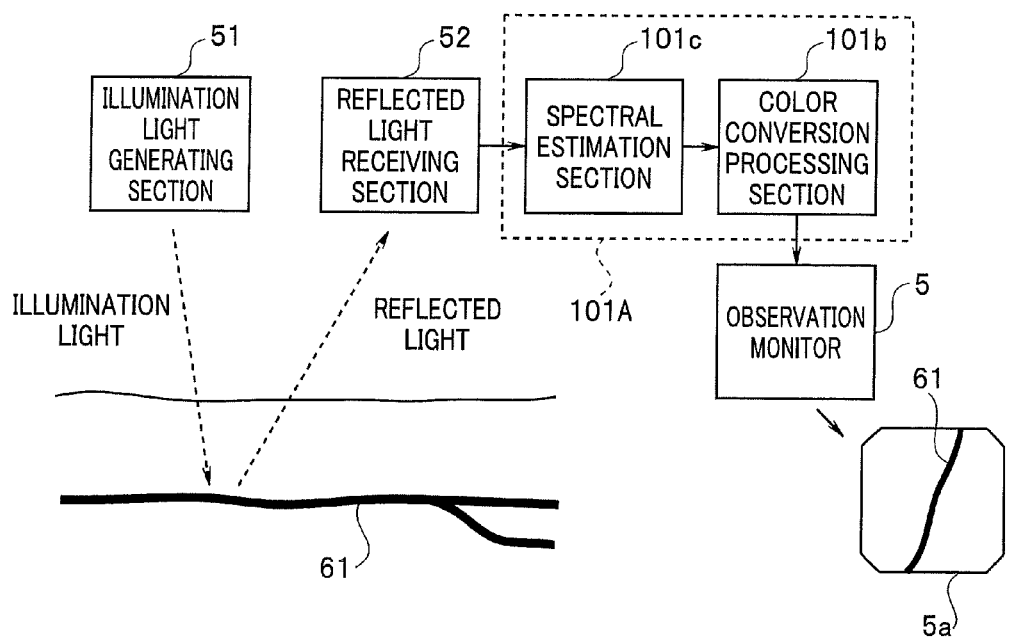
FIG. 17 is a diagram for illustrating a whole process flow in narrowband light observation according to the second embodiment of the present invention.

FIG. 17 is a diagram for illustrating a whole process flow in the narrowband light observation according to the present embodiment. In FIG. 17, the same components as in FIG. 3 are denoted by the same reference numerals and signs and description thereof is omitted. The image processing section 101A includes a spectral estimation section 101c in addition to the color conversion processing section 101b. That is, the image processing section 101A constitutes image output means or an image output section that generates and outputs a first image signal by performing spectral estimation processing for an image pickup signal of a return light. Here, the spectral estimation section 101c extracts a spectral estimation image signal e1 near the wavelength of 600 nm, a spectral estimation image signal e2 near the wavelength of 630 nm and a spectral estimation image signal e3 near the wavelength of 540 nm from three images of RGB by spectral estimation processing and outputs the signals to the color conversion processing section 101b.

More specifically, the spectral estimation section 101c calculates n-dimensional spectral images from three inputs by matrix operations on the basis of a priori information given in advance, and selectively outputs e1, e2 and e3 among calculated n-dimensional spectral estimation image signals. The spectral estimation section 101c is configured to calculate and output the spectral estimation image signal e1 near the wavelength of 600 nm, the spectral estimation image signal e2 near the wavelength of 630 nm and the spectral estimation image signal e3 near the wavelength of 540 nm using matrix operations and the like.

Subsequent processing in the color conversion processing section 101b for the first, second and third spectral estimation image signals outputted from the spectral estimation section 101c is the same as the processing described in the first embodiment described above.

Figure 18:
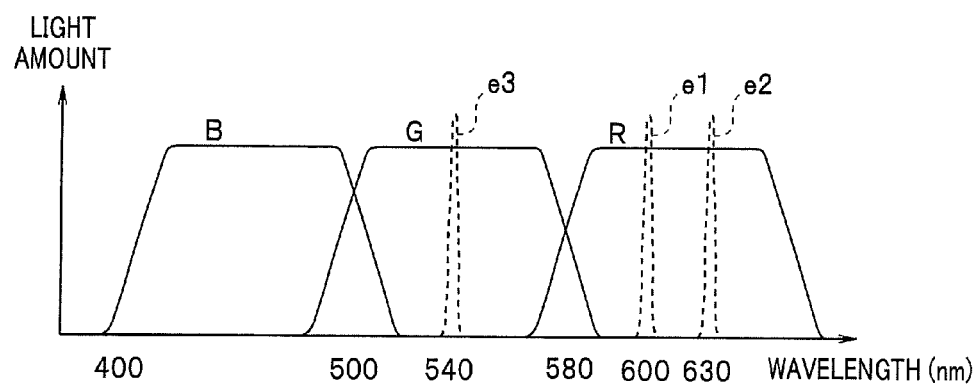
FIG. 18 is a diagram showing a spectral characteristic for illustrating a case of estimating three narrowband-light spectral image signals e1, e2 and e3 from three broadband-light image signals B, G and R according to the second embodiment of the present invention.

FIG. 18 is a diagram showing a spectral characteristic for illustrating a case of estimating the three narrowband-light spectral image signals e1, e2 and e3 from three broadband-light image signals B, G and R. The three broadband lights B, G and R in FIG. 18 are obtained by the color filters of the image pickup device 2A, and image signals of the three broadband lights B, G and R are inputted to the spectral estimation section 101c.

The spectral estimation section 101c estimates at least one narrowband-light spectral estimation image signal e1 from the three broadband-light image signals B, G and R by spectral estimation processing. Here, the spectral estimation image signal e1 near the wavelength of 600 nm, the spectral estimation image signal e2 near the wavelength of 630 nm and the spectral estimation image signal e3 near the wavelength of 540 nm are obtained from the broadband-light image signals B, G and R having wavelength bands as shown in FIG. 18 by spectral estimation processing. Here, two narrowband-light spectral estimation image signals e1 and e2 within the wavelength band R between the maximum value ACmax and the minimum value ACmin in FIG. 4 and a spectral estimation image signal e3 outside the wavelength band R are obtained by spectral estimation, and the spectral estimation image signals e1, e2 and e3 are supplied to the color conversion processing section 101b.

Note that at least one spectral estimation image signal e1 (here, the three spectral image signals e1, e2 and e3) may be obtained from image signals of two broadband lights among the three broadband lights, for example, image signals of the broadband lights G and R by spectral estimation processing.

Figure 19:
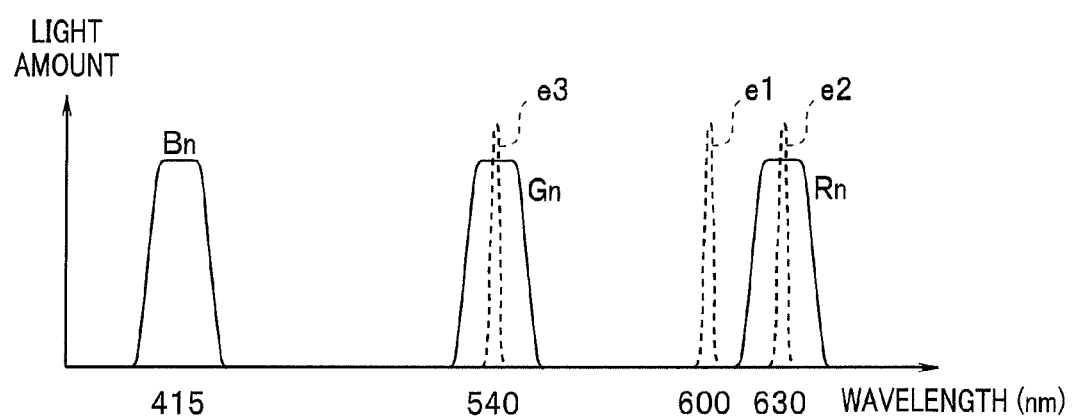
FIG. 19 is a diagram showing a spectral characteristic for illustrating a case of estimating three narrowband-light spectral estimation image signals e1, e21 and e31 from image signals of three narrowband lights, Bn, Gn and Rn according to the second embodiment of the present invention.

Furthermore, the spectral estimation image signal e1 (here, the three spectral estimation image signals e1, e2 and e3) may be obtained not from image signals of the broadband lights shown in FIG. 18 but from image signals of narrowband lights as shown in FIG. 19 by spectral estimation processing.

FIG. 19 is a diagram showing a spectral characteristic for illustrating a case of estimating spectral estimation image signals e1, e2 and e3 of the three narrowband lights from image signals of three narrowband lights Bn, Gn and Rn. As shown in FIG. 19, the spectral estimation section 101c estimates the three spectral estimation image signals, that is, the spectral estimation image signal e1 near the wavelength of 600 nm, the spectral estimation image signal e2 near the wavelength of 630 nm and the spectral estimation image signal e3 near the wavelength of 540 nm from the image signals Bn, Gn and Rn of the three narrowband lights.

Note that at least one spectral estimation image signal e1 may be obtained from at least one narrowband light and at least one broadband light by spectral estimation. That is, at least one of the three broadband lights in FIG. 18 may be a narrowband light, or at least one of the three narrowband lights in FIG. 19 may be a broadband light.

The three narrowband lights Bn, Gn and Rn may be obtained by the color filters of the image pickup device 2A having a spectral characteristic as shown in FIG. 18 or FIG. 19, or may be obtained by applying return lights of three illumination lights (that is, illumination lights of the narrowband lights Bn, Gn and Rn) generated with the use of a rotating filter as shown in FIG. 2 in the light source device, to a monochrome image pickup device.

Furthermore, note that image signals of the three (or two) broadband lights may be obtained not with the use of the color filters of the color image pickup device but by applying return lights of three (or two) illumination lights generated by arranging a first group of filters of a rotating filter having such a sensitivity characteristic that an image signal having a spectral characteristic as shown in FIG. 18 or FIG. 19 is obtained, on an optical path in the light source device, to a monochrome image pickup device.

Therefore, the same advantages as the endoscope apparatus 1 described above can be also obtained by the endoscope apparatus 1A of the present embodiment.

Figure 20:
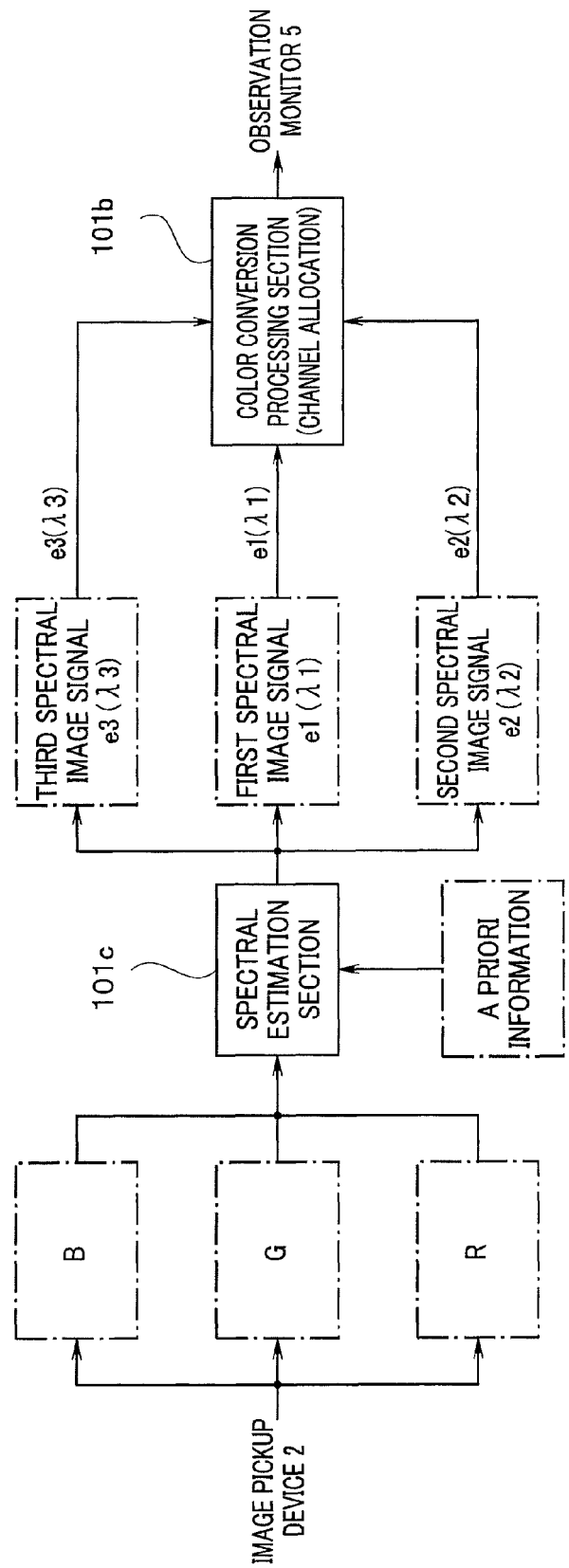
FIG. 20 is a diagram for illustrating a flow of processing for an image obtained from an image pickup device 2 in an image processing section 101A according to the second embodiment of the present invention.

FIG. 20 is a diagram for illustrating a flow of processing for an image obtained from the image pickup device 2 in an image processing section 101A according to the present embodiment.

As shown in FIG. 20, three images, that is, first to third image signals P1, P2 and P3 are inputted to the spectral estimation section 101c from the image pickup device 2. The spectral estimation section 101c estimates and generates three spectral estimation image signals e1, e2 and e3 from the inputted two or three image signals.

The color conversion processing section 101b performs color conversion processing by allocation of channels, for the first spectral estimation image signal e1, the second spectral estimation image signal e2 and the third spectral estimation image signal e3 and outputs the signals to the observation monitor 5.

Note that, as for the color filters provided on the surface of the image pickup device, RGB color filters have been described as an example in the present second embodiment, but the color filters may be complementary color filters.

In the endoscope of the present embodiment also, a relatively thick blood vessel existing in a relatively deep part of a living mucosa is clearly displayed on the screen of the observation monitor 5 by performing the color conversion processing described above. Therefore, the surgeon can perform desired treatment such as ESD, looking at and confirming the relatively thick blood vessel.

Since the endoscope apparatus 1A described above is capable of displaying a blood vessel existing in a part near the epithelium of a living mucosa using the third spectral estimation image signal e3, the surgeon can use an endoscopic image on the screen of the observation monitor 5 not only for treatment but also for diagnosis of living tissue, for example, diagnosis of existence of cancer or range diagnosis for identifying a range of cancer, and for discrimination diagnosis for judging whether an affected part is benignant or malignant, from a state of capillary vessels, for example, degree of concentration or dispersion of the capillary vessels. Furthermore, it is possible to perform invasive depth diagnosis and the like taking into account of a blood vessel in a deeper part.

The wavelength of the second spectral estimation image e2 shown in FIG. 18 or FIG. 19 may be a light with a longer wavelength band than the minimum value ACmin of the absorption characteristic of hemoglobin in FIG. 4 (here, an absorption coefficient at the wavelength of 730 nm). That is, for the wavelength of the second spectral estimation image e2, such a wavelength band that the absorption coefficient is lower than the wavelength of the first spectral estimation image e1 and the scattering characteristic of living tissue is suppressed, for example, 740 nm, 770 nm, 805 nm, 810 nm, 850 nm, 870 nm, 880 nm, 910 nm, 940 nm, 1020 nm or 1300 nm may be used to obtain advantages equal to those described above (for example, when the wavelength of the second spectral estimation image e2 is set to any wavelength from 740 nm to 1300 nm, the wavelength of the first spectral estimation image e1 is set to any wavelength equal to or longer than 576 nm and at least equal to or shorter than 630 nm).

Note that, in addition to the third spectral estimation image signal e3, fourth and fifth images obtained by further spectral estimation may be used, color-conversion processed and displayed on the observation monitor 5.

As described above, according to the present embodiment described above, it is possible to provide an endoscope apparatus capable of clearly displaying a blood vessel in a deep mucosa without complicated work of medicine administration being performed.

(Third Embodiment)

In the first embodiment, at least one narrowband light that includes the first narrowband light NL1 is actually radiated to living tissue as an illumination light, and the color conversion processing described above is performed for an image of a return light thereof. In the second embodiment, the three narrowband lights including the first narrowband light NL1 are not actually radiated to living tissue, but image information of a return light of each narrowband light is obtained by so-called spectral estimation. Then, color conversion processing as described above is performed for a spectral estimation image signal of each wavelength obtained by the spectral estimation. In the present third embodiment, the color conversion processing described above is performed for an image signal of a return light of an actual illumination light of a narrowband light and a spectral estimation image signal obtained by spectral estimation.

Figure 21:
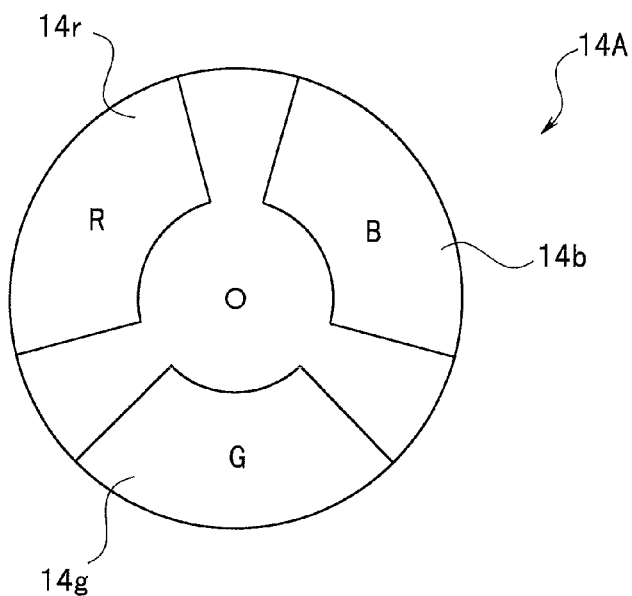
FIG. 21 is a diagram showing a configuration of a rotating filter 14A according to a third embodiment of the present invention.

A configuration of an endoscope apparatus 1B of the present embodiment is the same as the configuration of the endoscope apparatus 1 shown in FIG. 1, but a configuration of a rotating filter 14A of the present embodiment is different. FIG. 21 is a diagram showing the configuration of the rotating filter 14A according to the present embodiment. As shown in FIG. 21, the rotating filter 14A is merely provided with RGB filter sections constituting a set of filters for outputting frame-sequential lights having a spectral characteristic for the normal light observation mode. Return lights of the frame-sequential BGR lights are received by a monochrome image pickup device 2.

Figure 22:
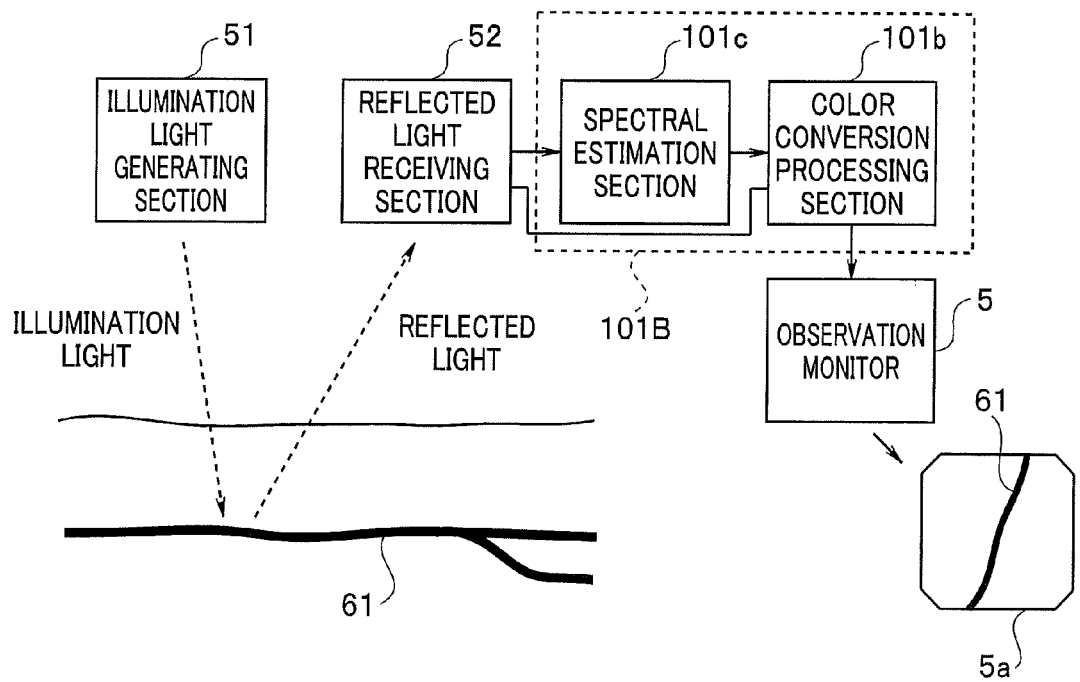
FIG. 22 is a diagram for illustrating a whole process flow in a special light observation mode according to the third embodiment of the present invention.

FIG. 22 is a diagram for describing a whole process flow in a special light observation mode according to the present embodiment. In FIG. 22, the same components as shown in FIG. 17 are denoted by the same reference numerals and signs and description thereof is omitted. An image processing section 101B includes the color conversion processing section 101b and the spectral estimation section 101c. The spectral estimation section 101c generates at least one spectral estimation image signal e from two or three image signals among RGB, and color conversion processing for one image signal among RGB and the spectral estimation image signal is performed.

Here, more specifically, a first spectral estimation image signal e1 near the wavelength of 600 nm and a third spectral estimation image signal e3 near the wavelength of 540 nm are estimated from the three (or two) image signals among RGB by spectral estimation and outputted to the color conversion section 101b.

Figure 23:
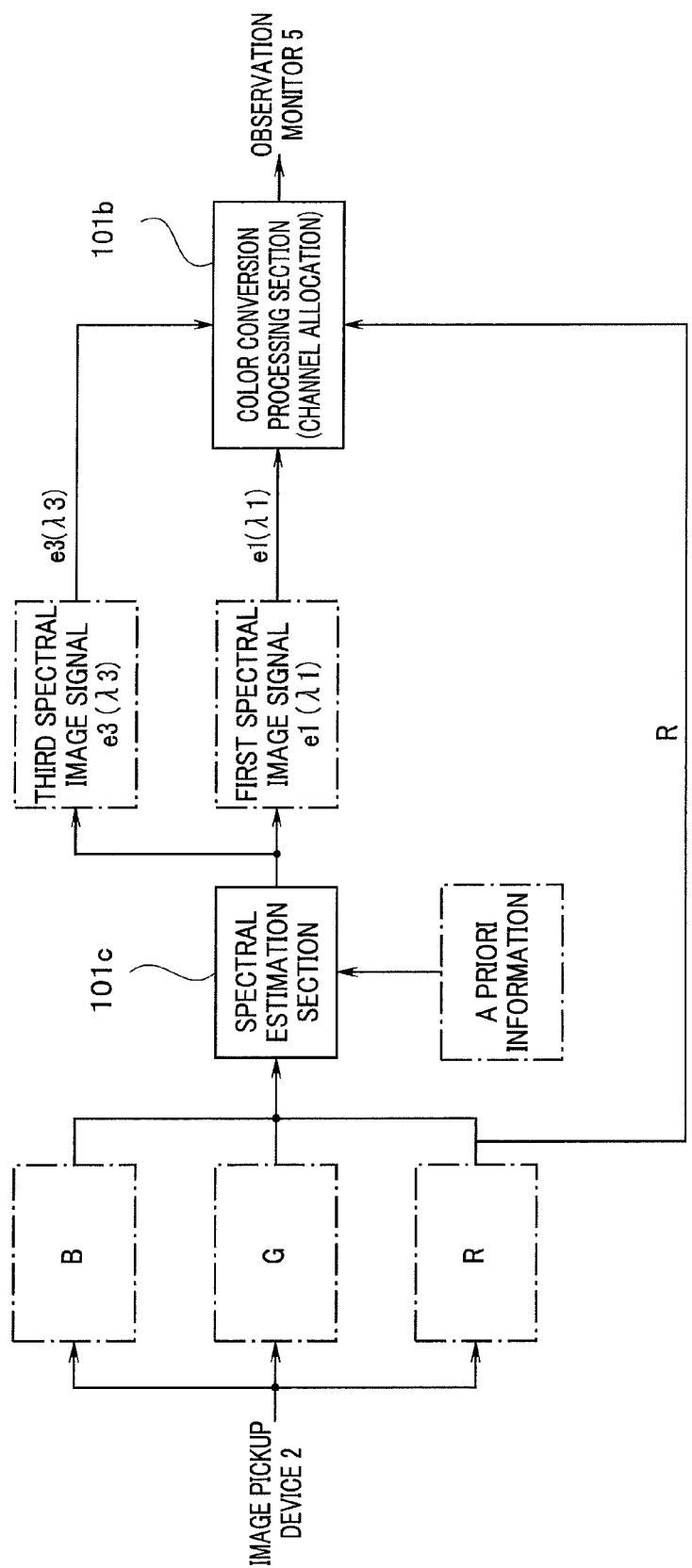
FIG. 23 is a diagram for illustrating a flow of processing for an image obtained from an image pickup device 2 in an image processing section 101B according to the third embodiment of the present invention.

FIG. 23 is a diagram for illustrating a flow of processing for an image obtained from the image pickup device 2 in the image processing section 101B according to the present embodiment.

As shown in FIG. 23, three images, that is, first to third image signals B, G and R are inputted to the spectral estimation section 101c from the image pickup device 2. The spectral estimation section 101c estimates and generates the two spectral estimation image signals e1 and e3 from the inputted two or three images.

The color conversion processing section 101b performs color conversion processing by allocation of channels, for the spectral estimation image signal e1, the spectral estimation image signal e3 and the image signal R and outputs the signals to the observation monitor 5.

Note that the processing in the color conversion processing section 101b is similar to that of the first embodiment.

Figure 24:
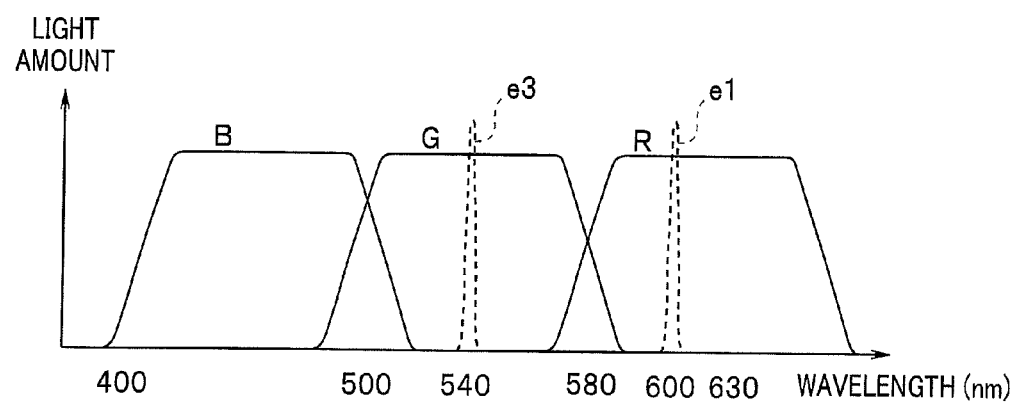
FIG. 24 is a diagram showing a spectral characteristic for illustrating a case of estimating at least one narrowband-light spectral estimation image signal e1 from three (or two) broadband-light image signals B, G and R according to the third embodiment of the present invention.

FIG. 24 is a diagram showing a spectral characteristic for illustrating a case of estimating at least one narrowband-light spectral estimation image signal e1 from the three (or two) broadband-light image signals B, G and R. Note that, here, the two narrowband-light spectral estimation image signals e1 and e3 are estimated from the three broadband-light image signals B, G and R.

Then, as shown in FIG. 23, the spectral estimation section 101c performs spectral estimation of and generates the spectral image signals e1 and e3 by signal processing on the basis of at least two image pickup signals of return lights from a subject (here, the three image pickup signals B, G and R).

The spectral estimation image signals e1 and e3 outputted from the spectral estimation section 101c and the real image signal R are inputted to the color conversion processing section 101b. As described above, the processing in the color conversion processing section 101b is the same as the processing described in the above first embodiment.

Thus, if only the spectral image signal e1 obtained by spectral estimation is color-conversion-processed to be monochromatically displayed as described above, a thick blood vessel 61 under a mucosa can be clearly displayed. If at least one of the other two image signals, that is, the spectral estimation image signal e3 and the real image signal R, is included to be color-conversion-processed and displayed, it is possible to display not only the thick blood vessel 61 under a mucosa but also capillary vessels in an epithelium and a thick blood vessel in a deeper part on the observation monitor 5 together.

Note that, though the third image signal near the wavelength of 540 nm is obtained by spectral estimation in the example described above, the second image signal near the wavelength of 630 nm may be obtained by spectral estimation, and an image signal B may be used as a real image.

Furthermore, an illumination light for obtaining a real image signal may be the narrowband light described with reference to FIG. 19.

Furthermore, note that the three broadband lights B, G and R in FIG. 23 may be obtained by the color filters of the image pickup device 2A. That is, the three broadband lights B, G and R may be obtained with the use of the light source device 4A as described in the second embodiment and the color filters of the image pickup device 2A.

Therefore, the same advantages as the endoscope apparatuses 1 and 1A described above can be also obtained by the endoscope apparatus 1B of the present embodiment.

Note that, though RGB color filters have been described as an example of a case of using color filters provided on the surface of the image pickup device in the present third embodiment, the color filters may be complementary color filters.

In the endoscope of the present embodiment also, a relatively thick blood vessel existing in a relatively deep part of a living mucosa is clearly displayed on the screen of the observation monitor 5 by performing the processing described above. Therefore, the surgeon can perform desired treatment such as ESD, looking at and confirming the relatively thick blood vessel.

Since the endoscope apparatus 1A described above is capable of displaying a blood vessel existing in a part near an epithelium of a living mucosa using the spectral estimation image e3 corresponding to the third narrowband light NL3 or the narrowband light Gn, the surgeon can use an endoscopic image on the screen of the observation monitor 5 not only for treatment but also for diagnosis of living tissue, for example, diagnosis of existence of cancer or range diagnosis for identifying a range of cancer, and for discrimination diagnosis for judging whether an affected part is benignant or malignant, for example, from degree of concentration or dispersion of capillary vessels. Furthermore, it is possible to perform invasive depth diagnosis and the like taking into account of a blood vessel in a deeper part.

The wavelength of the second narrowband light NL2 or the second spectral estimation image signal e2 may be a light of a longer wavelength band than the minimum value ACmin of the absorption characteristic of hemoglobin in FIG. 4 (here, an absorption coefficient at the wavelength of 730 nm). That is, as for the wavelength of the second narrowband light NL2 or the second spectral estimation image signal e2, such a wavelength band that the absorption coefficient is lower than the wavelength of the first narrowband light NL1 or the first spectral estimation image signal e1 and the scattering characteristic of living tissue is suppressed, for example, 740 nm, 770 nm, 805 nm, 810 nm, 850 nm, 870 nm, 880 nm, 910 nm, 940 nm, 1020 nm or 1300 nm can be used to obtain advantages equal to those described above (for example, when the wavelength of the second narrowband light NL2 or the second spectral estimation image signal e2 is set to any wavelength from 740 nm to 1300 nm, the wavelength of the first narrowband light NL1 or the first spectral estimation image signal e1 is set to any wavelength equal to or longer than 576 nm and equal to or shorter than 630 nm).

As described above, according to the present embodiment described above, it is possible to provide an endoscope apparatus capable of clearly displaying a blood vessel in a deep mucosa without complicated work of medicine administration being performed.

(Common Modification of Respective Embodiments)
(First Modification)

In the three embodiments and each of modifications thereof described above, the light absorption characteristic of venous blood is given as an example, and two narrowband lights are selected on the basis of the characteristic. However, at least two narrowband lights as described above may be selected on the basis of the light absorption characteristic of arterial blood or the light absorption characteristic of blood of combination of venous blood and arterial blood.

(Second Modification)

In the endoscope apparatus of each embodiment and each modification (including the modification of each embodiment) described above, the light near the wavelength of 600 nm and the light near the wavelength of 630 nm are used as the wavelengths of the first narrowband light NL1 and the second narrowband light NL2, respectively. Preferably, the first narrowband light NL1 and the second narrowband light NL2 are a narrowband light with a wavelength within a wavelength range from 580 to 620 nm having a distribution in a range of a predetermined width and a narrowband light with a wavelength within a wavelength range from 610 to 730 nm having a distribution in a range of a predetermined width, respectively. More preferably, they are a narrowband light with a wavelength within a wavelength range from 585 to 615 nm having a distribution in a range of a predetermined width and a narrowband light with a wavelength within a wavelength range from 620 to 640 nm having a distribution in a range of a predetermined width, respectively.

Therefore, if the first narrowband light NL1 and the second narrowband light NL2 are lights with wavelengths having an absorption characteristic as described above between a maximum value and minimum value of absorption characteristic, the wavelengths of the first narrowband light NL1 and the second narrowband light NL2 are not limited to the light near the wavelength of 600 nm and the light near the wavelength of 630 nm, respectively, and lights with any wavelength are possible. For example, as the wavelengths of the first narrowband light NL1 and the second narrowband light NL2, the light near the wavelength of 610 nm and the light near a wavelength of 645 nm, or the light near the wavelength of 630 nm and the light near a wavelength of 660 nm may be used, respectively.

(Third Modification)

In the endoscope apparatus of each embodiment and each modification (including the modification of each embodiment) described above, the light near the wavelength of 540 nm is used to display capillary vessels in an epithelium of living tissue, as the third narrowband light NL3. However, the wavelength of the third narrowband light NL3 is not limited thereto. For example, as the wavelength of the third narrowband light NL3, the light near the wavelength of 415 nm or 460 nm shorter than the wavelength 540 nm may be used. Especially, in order to obtain information about an epithelium of living tissue, the light near the shorter wavelength of 415 nm or 460 nm is more desirable than the light near the wavelength of 540 nm.

(Fourth Modification)

It has been described that a heat light source lamp, an LED, an LD or the like is used for the light source device of each embodiment and each modification (including the modification of each embodiment) described above. However, other means may be used. For example, a tunable laser may be used as light source means or a light source section. A broadband light generated by exciting a fluorescent body with an LED or an LD may be used.

(Fifth Modification)

In the case of radiating a narrowband light in the endoscope apparatus of each embodiment and each modification (including the modification of each embodiment) described above, it is possible to generate, for example, the narrowband light near the wavelength of 600 nm by a laser, and the narrowband light near the wavelength of 630 nm by an LED. It is also possible to generate the narrowband light near the wavelength of 600 nm by an LED, and the narrowband light near the wavelength of 630 nm by a laser. By using a laser beam, it is possible to reduce noise in a depth direction.

(Sixth Modification)

In each embodiment and each modification (including the modification of each embodiment) described above, a relatively thick blood vessel in a deep mucosa is clearly displayed by an image of a narrowband light near the wavelength of 600 nm. In order to clearly display a blood vessel in a deeper part, it may be made possible to use an image of a narrowband light with a longer wavelength. Though display on the observation monitor 5 is performed by the combination of the narrowband lights near the wavelength of 600 nm and near the wavelength of 630 nm described above, other combinations may be prepared in advance in that case so that the surgeon can select a desired combination from among the multiple combinations.

As combinations of two display images, the endoscope 1 (or 1A, or 1B) has a first combination using a first image signal NL1 near the wavelength of 600 nm and a second image signal NL2 near the wavelength of 630 nm and a second combination using a first image signal NL12 near the wavelength of 650 nm and a second image signal NL22 near a wavelength of 680 nm, and the surgeon selects a desired combination between the two combinations.

According to such a configuration, the surgeon can cause a blood vessel at a desired depth to be clearly displayed, changing the blood vessel depth by selecting a combination and can cause a blood vessel in a deeper part to be displayed together by the second image signal to perform observation.

Figure 25:
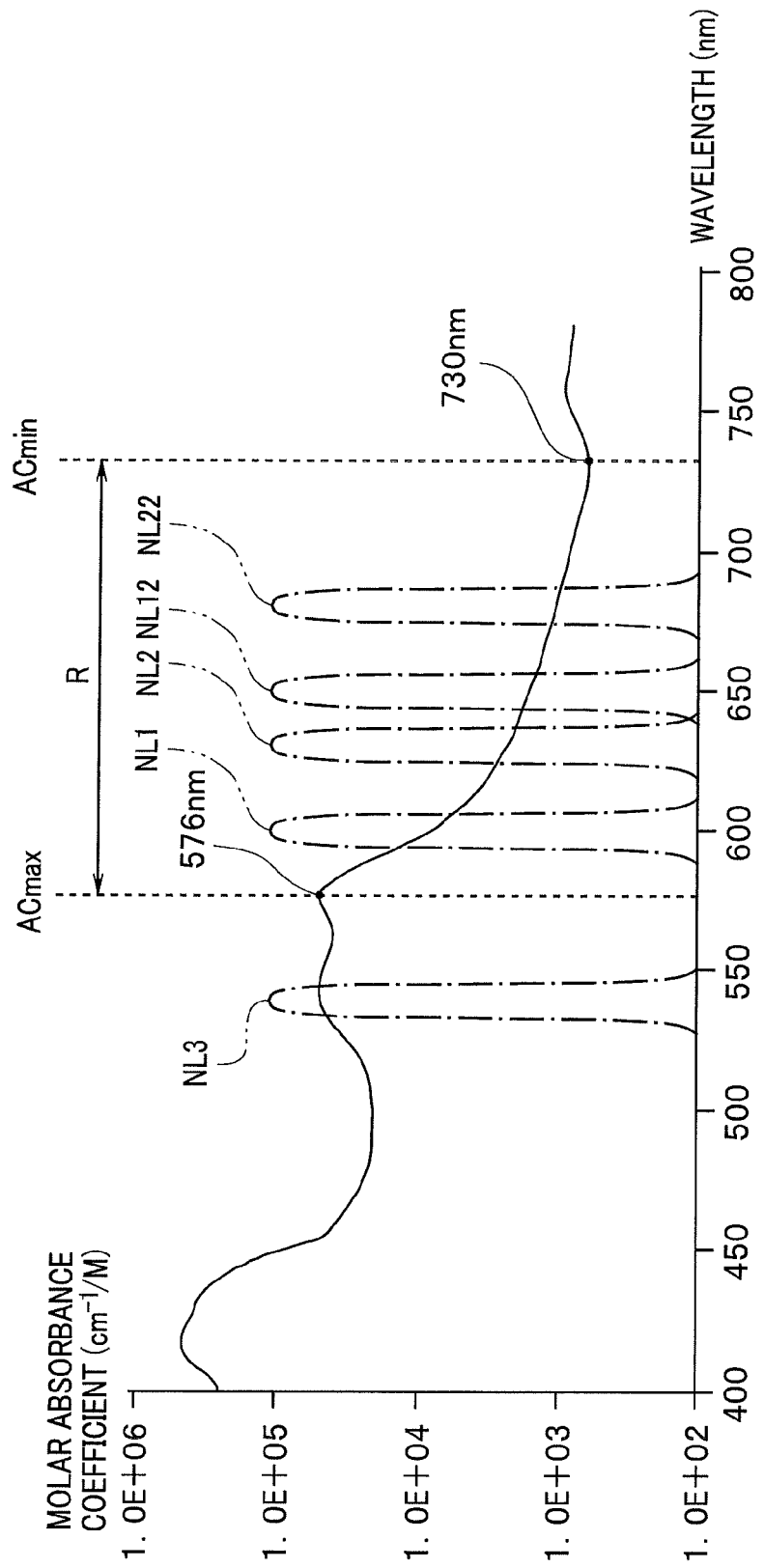
FIG. 25 is a diagram showing the light absorption characteristic of venous blood for illustrating a sixth modification.

FIG. 25 is a diagram showing the light absorption characteristic of venous blood for illustrating the present sixth variation. In FIG. 25, one of the two combinations is a first combination of the narrowband light NL1 near the wavelength of 600 nm and the narrowband light NL2 near the wavelength of 630 nm. The other is a second combination of a narrowband light NL12 near the wavelength of 650 nm and a narrowband light NL22 near the wavelength of 680 nm. The user can select which combination is to be selected. For example, the user can select by which combination display should be performed, by selecting a mode.

Note that, as another combination, a combination of a narrowband light near a wavelength of 615 nm and a narrowband light near the wavelength of 645 nm, a combination of a narrowband light near the wavelength of 630 nm and a narrowband light near the wavelength of 660 nm or the like is possible.

In the case of the second combination, since the wavelength used is shifted to the long wavelength side in comparison with the first combination, an image of a deeper part is clearly displayed. Therefore, if blood, bile, urine or the like adheres to a mucosal surface of a living body when the surgeon wants to display a blood vessel in a deeper part, a blood vessel at a desired depth can be clearly displayed by selecting the second combination.

It is desirable that two wavelengths of the respective combinations have almost the same wavelength difference so that similar contrast can be obtained.

Two or more combinations can be realized by increasing the number of combinations of rotating filters in the light source device or increasing the number of spectral estimation image signals estimated by spectral estimation processing.

As combinations of narrowband light wavelengths, it is desirable to have two combinations of a combination of a narrowband light near a wavelength of 580 nm and a narrowband light near the wavelength of 630 nm, and a combination of a narrowband light near the wavelength of 590 nm and a narrowband light near the wavelength of 630 nm in the case of clearly displaying a blood vessel at a relatively shallow position from a mucosal surface.

As combinations of narrowband light wavelengths, it is desirable to have two combinations of a combination of a narrowband light near the wavelength of 600 nm and a narrowband light near the wavelength of 630 nm, and a combination of a narrowband light near the wavelength of 650 nm and a narrowband light near the wavelength of 680 nm in the case of clearly displaying a blood vessel at a deeper position from a mucosal surface or a blood vessel under a mucosa under blood or the like.

Though two combinations are used in the example described above, three or more combinations are also possible. In the case of three, for example, the three are a first combination of a narrowband light near the wavelength of 600 nm and a narrowband light near the wavelength of 630 nm, a second combination of a narrowband light near the wavelength of 650 nm and a narrowband light near the wavelength of 680 nm, and a third combination of a narrowband light near a wavelength of 700 nm and a narrowband light near the wavelength of 730 nm.

Since multiple display results can be obtained as described above, the surgeon can cause a desired blood vessel to be clearly displayed by selecting a combination on a longer wavelength side (for example, a combination of narrowband lights near the wavelength of 650 nm and near the wavelength of 680 nm) when the concentration of blood or the like adhering to a mucosal surface of a living body is high, and selecting a combination on a shorter wavelength side (for example, a combination of narrowband lights near the wavelength of 580 nm and near the wavelength of 630 nm) when a blood vessel exists in a relatively shallow part or when the concentration of blood or the like adhering to a mucosal surface of a living body is low.

(Seventh Modification)

In each embodiment and each modification (including the modification of each embodiment) described above, wavelength difference between two narrowband lights of the first narrowband light NL1 and the second narrowband light NL2 is fixed. However, it is possible to cause one to be fixed and the other to be variable. For example, in the case of the narrowband light near the wavelength of 600 nm and the narrowband light near the wavelength of 630 nm, it is possible to fix the narrowband light near the wavelength of 600 nm and cause the other narrowband light to be variable from near the wavelength of 630 nm to near the wavelength of 730 nm and set arbitrarily. Otherwise, it is also possible to fix the other narrowband light near the wavelength of 730 nm and cause a narrowband light from near the wavelength of 590 nm to near a wavelength of 620 nm to be variably and arbitrarily set. Note that it is also possible to fix the narrowband light near the wavelength of 600 nm and cause the other narrowband light to be arbitrarily set in a wavelength band equal to or more than 730 nm.

By fixing one of two narrowband lights and causing the other to be variable, it is possible to display a blood vessel in a desired area more clearly.

(Eighth Modification)

In each embodiment and each modification (including the modification of each embodiment) described above, three images are obtained to display a narrowband light image on the observation monitor 5. However, a fourth image may be obtained so that a display image is generated by appropriately selecting images from among four images.

The endoscope apparatus has the narrowband light observation mode in addition to the normal light observation mode, and the surgeon switches the normal light observation mode to the narrowband light observation mode as necessary to perform various treatments. By adding the fourth image, it is possible to easily obtain a display image of each observation mode.

For example, a light source device capable of radiating an illumination light of a blue narrowband light (a broadband light is also possible) with a wavelength shorter than the wavelength of 540 nm is used to obtain the fourth image. The light source device alternately radiates an illumination light of a first combination of a light with the fourth wavelength and a narrowband light near the wavelength of 600 nm, and a second combination of a narrowband light near the wavelength of 540 nm and a narrowband light near the wavelength of 630 nm to a subject. Note that an illumination light of a combination of the light with the fourth wavelength, the narrowband light near the wavelength of 540 nm and the narrowband light near the wavelength of 600 nm, and an illumination light of the narrowband light near the wavelength of 630 nm may be alternately radiated to a subject.

Then, a return light of each illumination light is received by the image pickup device having the RGB color filters. For example, an image of a return light of the narrowband light with the fourth wavelength is picked up in the B band of the color filters, and an image of a return light of the narrowband light near the wavelength of 600 nm is picked up in the R band. Note that the color filters of the image pickup device may be complementary ones. Furthermore, note that the image pickup device may be a monochrome image pickup device.

Since images of the respective bands are separated from each other, four monochrome images are obtained in the video processor 7. Note that appropriate color balance adjustment is performed for an image signal of each light to obtain each image.

Then, in the video processor 7, a normal image for the normal light observation mode is generated with the use of images of the four return lights of the light with the fourth wavelength, the narrowband light near the wavelength of 540 nm, the narrowband light near the wavelength of 600 nm and the narrowband light near the wavelength of 630 nm.

In the video processor 7, a first narrowband light image is generated by allocating an image signal of the light with the fourth wavelength to the B and G channels, allocating an image signal of the narrowband light near the wavelength of 540 nm to the R channel, and using two images of the light with the fourth wavelength and the narrowband light near the wavelength of 540 nm.

Furthermore, in the video processor 7, a second narrowband light image is generated with the use of three images of the narrowband light near the wavelength of 540 nm, the narrowband light near the wavelength of 600 nm and the narrowband light near the wavelength of 630 nm.

Note that an image signal of the narrowband light near the wavelength of 600 nm is displayed with high contrast.

Then, in response to an image display instruction by the surgeon, an image generated as described above is selected and displayed on the observation monitor 5.

According to such a configuration, it is possible to display a normal image for the normal light observation and a narrowband light image for the narrowband light observation at the same time or display the normal image and the narrowband light image being overlapped. For example, it is possible to display a normal light image and a first narrowband light image (or a second narrowband light image) in parallel or display the first narrowband light image and the second narrowband light image in parallel.

Furthermore, by allocating an image signal of the light with the fourth wavelength to the B channel, an image signal of the narrowband light near the wavelength of 540 nm to the G channel, and an image signal of the narrowband light near the wavelength of 600 nm to the R channel, or by allocating the image signal of the light with the fourth wavelength to the B channel, the image signal of the narrowband light near the wavelength of 540 nm and the image signal of the narrowband light near the wavelength of 600 nm to the G channel, and the image signal of the narrowband light near the wavelength of 600 nm (or the image signal of the narrowband light near the wavelength of 600 nm and an image signal of the narrowband light near the wavelength of 630 nm) to the R channel, it is possible to generate an overlap image obtained by adding information about a blood vessel in a deep part to a normal image and display the image on the observation monitor 5.

Furthermore, by allocating the image signal of the light with the fourth wavelength to the B channel, the image signal of the light with the fourth wavelength and the image signal of the narrowband light near the wavelength of 600 nm to the G channel, and the image signal of the narrowband light near the wavelength of 600 nm (or the image signal of the narrowband light near the wavelength of 600 nm and the image signal of the narrowband light near the wavelength of 630 nm) to the R channel, it is possible to generate an image in which both of a blood vessel in an epithelium and a blood vessel in a deep part are shown with high contrast and display the image on the observation monitor 5.

Note that the image signal with the fourth wavelength may be generated by spectral estimation.

As described above, according to the present eighth modification, parallel display or overlap display of a normal image and a narrowband light image becomes possible.

(Ninth Modification)

Furthermore, the endoscope apparatus according to each embodiment and each modification (including the modification of each embodiment) described above may be used to cause a normal light image for the normal light observation mode and a narrowband light image for the narrowband light observation mode to be displayed in parallel.

For example, in the case of performing treatment such as ESD, a narrowband light image for the narrowband light observation mode for clearly displaying a thick blood vessel in a deep mucosa can be displayed on the observation monitor 5 after the surgeon identifies a lesioned part until the lesioned part is dissected and ablated. Note that, after the surgeon identifies a lesioned part until he dissects and ablates the lesioned part, a narrowband light image for the narrowband light observation mode and a normal light image for the normal light observation mode may be displayed on the observation monitor 5 in parallel.

The surgeon performs hemostasis treatment, looking at a narrowband light image (or parallel display of a narrowband light image and a normal light image) displayed on the observation monitor 5. As described above, there may be a bleeding point under blood during bleeding. Therefore, there may be a case where it is better to perform hemostasis treatment, looking at a narrowband light image.

When a narrowband light image and a normal light image are displayed in parallel, the surgeon can confirm a state of hemostasis after finishing the hemostasis treatment, looking at the normal light image. When only the narrowband light image is displayed, the surgeon can confirm the state of hemostasis after finishing the hemostasis treatment by changing the mode of the endoscope apparatus to the normal light observation mode and displaying the normal light image on the observation monitor 5.

Conventionally, normal light observation by an image under a white color light and conventional narrowband light observation using narrowband lights near the wavelengths of 415 nm and 540 nm have been performed. By adding the new narrowband light observation mode for clearly displaying a blood vessel in a deep mucosa according to each embodiment and each modification (including the modification of each embodiment) described above, it is possible to perform, for example, invasive depth diagnosis of a lesion more effectively.

In endoscope diagnosis, observation of a lesioned part is performed. There may be a case where, while a normal light image or a conventional narrowband light image (an image corresponding to narrowband lights near the wavelengths of 415 nm and 540 nm) is displayed on the observation monitor 5, a lesioned part is enlargedly displayed to perform invasive depth diagnosis of the lesion.

In this case, conventionally, the surgeon enlarges the conventional narrowband light image (the image corresponding to the narrowband lights near the wavelengths of 415 nm and 540 nm) to perform the invasive depth diagnosis of the lesion.

However, by causing a new narrowband light image to be displayed on the observation monitor 5 together with the conventional narrowband light image using the endoscope apparatus according to each embodiment and each modification (including the modification of each embodiment) described above, the surgeon can perform the invasive depth diagnosis of the lesion with a higher accuracy.

Figure 26:
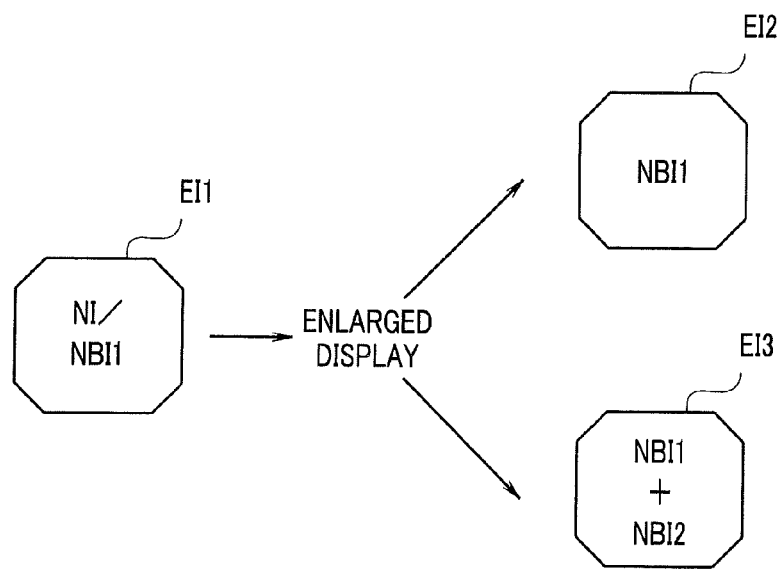
FIG. 26 is a diagram for illustrating an example of transition of image displays in enlargement observation in ninth modification.

FIG. 26 is a diagram for illustrating an example of transition of image display during enlargement observation of the ninth modification. First, the surgeon performs observation or diagnosis of a lesioned part, displaying a normal light image or a conventional narrowband light image (an image corresponding to narrowband lights near the wavelengths of 415 nm and 540 nm) EI1 on the observation monitor 5. It is possible not only to, by specifying enlarged display during the diagnosis, display an enlarged conventional narrowband light image (the image corresponding to the narrowband lights near the wavelengths of 415 nm and 540 nm) EI2 on the observation monitor 5 but also to display the conventional narrowband light image (the image corresponding to the narrowband lights near the wavelengths of 415 nm and 540 nm) EI1 and an image EI3 which includes the new narrowband light image (for example, an image corresponding to a narrowband light near the wavelength of 600 nm) by the surgeon's instruction.

This image EI3 may be an image in which the conventional narrowband light image (the image corresponding to the narrowband lights near the wavelengths of 415 nm and 540 nm) and the new narrowband light image (for example, an image corresponding to a narrowband light near the wavelength of 600 nm) are displayed in parallel or may be an image in which the conventional narrowband light image (the image corresponding to the narrowband lights near the wavelengths of 415 nm and 540 nm) and the new narrowband light image (for example, an image corresponding to a narrowband light near the wavelength of 600 nm) are overlappedly displayed.

Since the image EI3 includes an image of a blood vessel at a position deeper from a mucosal surface, the surgeon can perform invasive depth diagnosis of a lesion such as cancer with a higher accuracy.

As described above, according to each embodiment and each modification (including the modification of each embodiment) described above, it is possible to provide an endoscope apparatus capable of clearly displaying a blood vessel in a deep part of a mucosa without complicated work of medicine administration being performed.

The present invention is not limited to the embodiments described above, and various changes, alterations and the like are possible within a range not changing the spirit of the present invention.

What is claimed is:

1. An endoscope apparatus comprising:
a light source configured to radiate, to a part under an epithelium of a living mucosa of a subject, at least:
   a first light having a first wavelength band having a narrowband spectral characteristic in a range consisting essentially of a wavelength of 585 nm to a wavelength of 615 nm; and
   a second light having a second wavelength band having a narrowband spectral characteristic in a range consisting essentially of a wavelength of 610 nm to a wavelength of 730 nm; and
one or more processors comprising hardware, wherein the one or more processors are configured to:
   control an image sensor to:
      receive a first reflected light of the first light, and output a first image pickup signal based on the first reflected light;
      receive a second reflected light of the second light, and output a second image pickup signal based on the second reflected light; and
   output, to a display, at least:
      a first image signal for display based on the first image pickup signal; and
      a second image signal for display based on the second image pickup signal,
         wherein the first image signal for display is configured to be displayed to have a different visual characteristic than the second image signal for display.

2. The endoscope apparatus according to claim 1, wherein the second wavelength band has a narrowband spectral characteristic in a range consisting essentially of a wavelength of 620 nm to a wavelength of 640 nm.

3. The endoscope apparatus according to claim 1, wherein the one or more processors are configured to:
   allocate the first image signal for display to a first color channel in the display; and
   allocate the second image signal for display to a second color channel in the display, wherein the first color channel is different from the second color channel.

4. The endoscope apparatus according to claim 1, wherein the first wavelength band is selected such that:
   a hemoglobin absorption characteristic within the first wavelength band includes a first absorption coefficient; and
   a scattering characteristic of the living mucosa within the first wavelength band includes a first scattering coefficient;
wherein the second wavelength band is selected such that:
   the hemoglobin absorption characteristic within the second wavelength band includes a second absorption coefficient lower than the first absorption coefficient; and
   the scattering characteristic of the living mucosa within the second wavelength band includes a second scattering coefficient lower than the first scattering coefficient, and
wherein the first wavelength band and the second wavelength band are between a wavelength including a maximum absorption coefficient and a wavelength including a minimum absorption coefficient with regard to the hemoglobin absorption characteristic of the living mucosa of the subject.

5. The endoscope apparatus according to claim 4, wherein the light source is further configured to radiate:
   a third light having a third wavelength band outside a wavelength band from the wavelength including the maximum absorption coefficient to the wavelength including the minimum absorption coefficient with regard to the hemoglobin absorption characteristic of the living mucosa of the subject, and
wherein the one or more processors are configured to:
   control the image sensor to:
      receive a third reflected light of the third light, and output a third image pickup signal based on the third reflected light; and
   output, to the display:
      a third image signal for display based on the third image pickup signal,
         wherein the third image signal for display is configured to be displayed to have a different visual characteristic than the first image signal for display and the second image signal for display.

6. The endoscope apparatus according to claim 5, wherein the one or more processors are configured to:
   allocate the first image signal for display to a green color channel of the display;
   allocate the second image signal for display to a red color channel of the display; and
   allocate the third image signal for display to a blue color channel of the display.

* * * * *